(12) United States Patent
Sims

(10) Patent No.: US 10,010,693 B2
(45) Date of Patent: Jul. 3, 2018

(54) MEDICAL TUBING

(75) Inventor: David John Sims, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1136 days.

(21) Appl. No.: 14/128,515

(22) PCT Filed: Jun. 28, 2012

(86) PCT No.: PCT/NZ2012/000111
§ 371 (c)(1),
(2), (4) Date: May 5, 2014

(87) PCT Pub. No.: WO2013/002655
PCT Pub. Date: Jan. 3, 2013

(65) Prior Publication Data
US 2014/0236083 A1   Aug. 21, 2014

Related U.S. Application Data

(60) Provisional application No. 61/502,205, filed on Jun. 28, 2011.

(51) Int. Cl.
*F24H 1/10* (2006.01)
*A61M 16/10* (2006.01)
(Continued)

(52) U.S. Cl.
CPC ...... *A61M 16/1095* (2014.02); *A61M 13/003* (2013.01); *A61M 16/0816* (2013.01);
(Continued)

(58) Field of Classification Search
None
See application file for complete search history.

(56) References Cited

U.S. PATENT DOCUMENTS 2,876,801 A * 3/1959 November .............. F16L 11/15
138/121
3,163,707 A * 12/1964 Darling .................... A47L 9/24
128/204.18
(Continued)

FOREIGN PATENT DOCUMENTS

CN   1204266 A   1/1999
CN   1623612 A   6/2005
(Continued)

OTHER PUBLICATIONS

Supplementary European Search Report for Application No. EP 12 80 4642; dated Feb. 19, 2015; 4 pages.
(Continued)

*Primary Examiner* — Thor Campbell
(74) *Attorney, Agent, or Firm* — Knobbe Martens Olson & Bear LLP

(57) ABSTRACT

A medical tube has a tube wall, a first end and a second end. At least one heater wire is wrapped around the wall. Near or at one of the first end or the second end, there is at least one recess in an outer surface of the wall. The heater wire passes over the at least one tube recess such that the wire does not contact the wall in the area of the tube recess. Also disclosed are methods of making the tube and components used in making the tube.

25 Claims, 19 Drawing Sheets

(51) Int. Cl.
*A61M 16/08* (2006.01)
*A61M 13/00* (2006.01)
*F16L 53/38* (2018.01)

(52) U.S. Cl.
CPC .... *A61M 16/0841* (2014.02); *A61M 16/0875* (2013.01); *F16L 53/38* (2018.01); *A61M 2205/3368* (2013.01); *A61M 2207/00* (2013.01); *F04C 2270/0421* (2013.01)

(56) References Cited

U.S. PATENT DOCUMENTS

| | | | | |
|---|---|---|---|---|
| 3,891,007 | A * | 6/1975 | Kleykamp | F16L 11/111 138/121 |
| 4,342,612 | A * | 8/1982 | Lalikos | B29C 53/305 138/121 |
| 4,354,051 | A * | 10/1982 | Kutnyak | A47L 9/24 138/122 |
| 4,517,404 | A * | 5/1985 | Hughes | A47L 9/24 138/109 |
| 4,531,551 | A * | 7/1985 | Eichelberger | F16L 11/112 138/129 |
| 4,686,354 | A * | 8/1987 | Makin | A61M 16/1075 128/204.17 |
| 4,749,365 | A | 6/1988 | Magnifico et al. | |
| 5,357,948 | A * | 10/1994 | Eilentropp | A61M 16/08 128/203.26 |
| 5,600,752 | A * | 2/1997 | Lopatinsky | A61M 16/1075 138/114 |
| 5,640,951 | A * | 6/1997 | Huddart | A61M 16/08 128/203.26 |
| 5,894,865 | A * | 4/1999 | Winter | B29C 63/18 138/121 |
| 6,078,730 | A * | 6/2000 | Huddart | A61M 16/08 219/536 |
| 6,219,490 | B1 * | 4/2001 | Gibertoni | A61M 16/08 138/33 |
| 6,315,715 | B1 * | 11/2001 | Taylor | A61B 1/018 138/122 |
| 7,965,930 | B2 * | 6/2011 | Carlson | F16L 11/081 137/341 |
| 8,078,040 | B2 * | 12/2011 | Forrester | A61M 16/0875 392/481 |
| 8,563,864 | B2 * | 10/2013 | Carlson | F16L 11/081 137/341 |
| 8,657,270 | B2 * | 2/2014 | Takada | F16F 9/38 188/322.12 |
| 8,726,901 | B2 * | 5/2014 | Jassell | A61M 16/0875 128/200.24 |
| 8,905,082 | B2 * | 12/2014 | Gray | A61M 16/08 128/203.26 |
| 9,468,733 | B2 * | 10/2016 | Graham | A61M 16/0875 |
| 2003/0059213 | A1 | 3/2003 | Mackie et al. | |
| 2004/0087986 | A1 | 5/2004 | Ott | |
| 2010/0215351 | A1 | 8/2010 | Forrester | |
| 2013/0163970 | A1 * | 6/2013 | Schwarzkopf | F24H 1/0018 392/478 |
| 2013/0233318 | A1 * | 9/2013 | Graham | A61M 16/0875 128/205.27 |
| 2014/0037276 | A1 * | 2/2014 | Carlson | F16L 11/1185 392/468 |

FOREIGN PATENT DOCUMENTS

| | | |
|---|---|---|
| CN | 1662766 A | 8/2005 |
| CN | 1886866 A | 12/2006 |
| CN | 1947314 A | 4/2007 |
| CN | 101541367 A | 9/2009 |
| CN | 102025069 A | 4/2011 |
| EP | 0672430 A2 | 9/1995 |
| EP | 672430 A3 | 12/1995 |
| EP | 1352670 A1 | 10/2003 |
| EP | 1 369 141 A1 | 12/2003 |
| EP | 1902747 A2 | 3/2008 |
| GB | 2473531 A | 3/2011 |
| WO | WO 2011/162622 A1 | 12/2011 |

OTHER PUBLICATIONS

First Chinese Office Action for Chinese Patent Application No. 201280041821.9 dated Aug. 4, 2015 in 19 pages (with English translation).

Third Chinese Office Action for Chinese Patent Application No. 201280041821.9 dated Dec. 19, 2016 in 6 pages (with English translation).

International Search Report; Application No. PCT/NZ2012/000111; dated Jun. 28, 2012.

* cited by examiner

MEDICAL TUBING

FIELD OF THE INVENTION

The present invention relates to components for medical circuits. In one particular aspect, the invention relates to heated breathing tubes for use in the inspiratory and/or expiratory limb of a breathing circuit. In another aspect the invention relates to a heated tube component for a surgical insufflation system.

BACKGROUND OF INVENTION

In assisted breathing, and particularly in medical applications such as artificial ventilation, gases having high levels of relative humidity are supplied and returned through flexible breathing tubes of a relatively restricted size typically between a range of approximately 10 mm to 35 mm diameter (covering both neonatal and adult applications). Continuous Positive Airway Pressure (CPAP) systems or positive pressure ventilation systems that provide patients suffering from obstructive sleep apnoea (OSA) with positive pressure breathing gases, also use this sort of breathing tubes for delivering (or removing) inspiratory (and/or expiratory) gases.

Such breathing tubes are ideally very light, resistant to kinking or pinching, to ensure the greatest performance and level of comfort for the patient. The relatively light weight of a breathing tube is important to reduce any forces applied to the patient interface by the weight of the tube. Similarly, breathing tubes must be flexible and able to bend easily to achieve a high level of patient comfort, which in turn, can improve patient compliance with therapy. However, extremely light and flexible breathing tubes may be weak and prone to excessive kinking and/or stretching which can interfere with the ventilation therapy. For example blocking/pinching of the breathing tube or excessive stretching may reduce the ventilators ability to accurately detect patient breaths and trigger appropriately.

Breathing gases inhaled/exhaled by a patient are preferably in a condition having humidity near saturation level and at close to body temperature (usually at a temperature between approximately 33° C. and 37° C.). These conditions present a significant risk of condensation forming in the breathing tubes which is highly undesirable. In order to minimise condensation formation and to ensure breathing gases are delivered at the appropriate elevated temperature, breathing tubes may include an associated heater to heat the breathing gases. The addition of a heater (usually in the form of a heater wire inside the tube) requires electrical connections and terminations to complete the electrical circuit and receive power. These additional requirements add significant complexity to the breathing tube, and are often completed manually.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention consists in the foregoing and also envisages constructions of which the following gives examples only.

SUMMARY OF THE INVENTION

It is an object of the present invention to provide a component that will at least go some way towards improving on the above or which will at least provide the public and/or the medical profession with a useful choice.

In a first aspect, the invention comprises a medical tube comprising a tube wall and having a first end and a second end. At least one heater wire is wrapped around the wall near or at one of the first end or the second end. At least one recess exists in the outer surface of the wall. The heater wire passes over the at least one tube recess such that the wire does not contact the wall in the area of the tube recess.

Preferably the wall is helically corrugated with alternating crests and troughs and the wall defines a least one helical track on an outer surface extending between the first and second ends. Preferably, the at least one heater wire is located in the at least one track.

Preferably at least one of the at least one tracks is associated with a crest of the corrugated wall.

Preferably at least one of the at least one tracks is associated with a trough of the corrugated wall.

Preferably, the tube further includes an end connector on at least one of the first end or the second end.

Preferably, the tube recess includes an insulation displacement connector therein and the insulation displacement connector is engaged on at least one heater wire.

Preferably, the end connector includes at least one connector recess aligned with the at least one tube recess.

Preferably, the insulation displacement connector is located at least partially in the connector recess.

Preferably, the tube includes more than one helical track and each helical track includes at least one heater wire.

Preferably, the tube recess includes an insulation displacement connector therein and the insulation displacement connector is engaged on at least two of the heater wires.

Preferably, the medical tube further includes an outer sheath.

Preferably, the sheath is supported on the crests.

Preferably, at least one end of the tube further comprises a transition region in which the helical corrugation transitions to a semi-annular corrugation near the end of the tube.

Preferably, the transition and semi-annular corrugation region provides a track for each heater wire.

Preferably, the tube includes at least one pinch feature in the track to capture and retain a respective heater wire in the track.

Preferably, the tube includes at least one pinch feature in the track to capture and retain a respective heater wire in the track.

Preferably, the tube includes at least one locating feature near an end, the locating feature extending radially away from the tube.

Preferably, the locating feature includes an undercut to at least partially capture the wire.

Preferably, the locating feature is near a patient end.

Preferably, the feature is on the wall of the tube.

Preferably, the tube includes an end connector and the locating feature is on the end connector.

Preferably, the tube further includes a wire support member at an end of the tube, the wire support member comprising a ring shaped body having at least one wire support finger extending parallel with an axis of the ring body and the wire support finger being located in the recess such that the wire support finger is between an outer surface of the tube and the wire and supports the wire in the recess away from the tube.

Preferably, the insulation displacement element is fitted over the wire support finger when engaging the wire.

Preferably, the wire support member includes a plurality of wire support fingers extending parallel with an axis of the ring body and spaced around the perimeter of the member.

Preferably, the tube includes a plurality of the recesses and each of the plurality of wire support fingers is located in a respective recess.

Preferably, the insulation displacement element exists in each the recess and is fitted over a respective wire support finger.

In a further aspect, the invention comprises a medical tube comprising a tube wall and having a first end and a second end. At least two runs of heater wire are wrapped around the wall in a multi helix arrangement. At least one insulation displacement bridging element is located near the first end and extends over a portion of the circumference of the tube. The bridging element engages two or more the runs to complete at least part of an electrical circuit.

Preferably, the wall is at least double helically corrugated with alternating crests and troughs defining a least two helical tracks on the outer surface extending between the first and second ends. The at least two heater wire runs are located in a respective track.

Preferably, the tube further comprises at least one insulation displacement terminal element located near the second end and extending over a portion of the circumference of the tube. The terminal element engages only one of the runs and provides a terminal of the circuit.

Preferably, the terminal is one of a spade terminal, a pin terminal, a socket terminal, and a loop terminal.

Preferably, the tube further comprises at least one further insulation displacement bridging element located near the second end and extending over a portion of the circumference of the tube. The bridging element engages two or more of the runs to complete at least part of an electrical circuit.

Preferably, the tube further comprises an end connector on at least one of the first end or the second end. The end connector receives and retains one or more of the insulation displacement elements.

Preferably, the end connector includes a socket aperture adapted to receive the insulation displacement terminal elements.

In a further aspect, the invention comprises an insulation displacement element comprising a channel body having a base and two side portions. A pair of aligned slots extend lengthwise of the body from a first open end and separate the two side portions from the base for a portion of the length of the body. The slots are shaped to displace outer insulation from a wire or wires pushed into the slots.

Preferably, the base and/or side portions are chamfered or shaped to guide a wire into engagement with the slots.

Preferably, the channel body has a substantially "U" shaped cross section.

Preferably, the "U" shape has a substantially flat bottom.

Preferably, a second end of the channel body is adapted to engage with a plug or socket.

Preferably, the base includes at the second end a slot extending lengthwise of the body for a portion of the length of the body.

Preferably, the base at the open end projects beyond the side portions.

In a further aspect, the invention comprises an insulation displacement element comprising a channel body having a base and two depending side portions. A pair of aligned slots, one in each side portion, extend perpendicularly of the base from a first open end. The slots are shaped to displace outer insulation from a wire or wires pushed into the slots.

Preferably, the side portions are chamfered or shaped to guide a wire into engagement with the slots at the open end.

Preferably, the channel body has a substantially "U" shaped cross section.

Preferably, the "U" shape has a substantially flat bottom.

Preferably, a first end of the channel body is adapted to engage with a plug or socket and the base at the first end projects beyond the side portions.

Preferably, the base includes at the first end a slot extending lengthwise of the body for a portion of the length of the base.

Preferably, each the side portion includes more than one aligned slot for receiving more than one wire.

In a further aspect, the invention comprises an insulation displacement element comprising a base. An arm includes a wire engaging portion resiliently attached to the base such that the wire engaging portion can be resiliently urged towards the base. The wire engaging portion includes at least one slot shaped to displace outer insulation from a wire or wires pushed into the slot.

Preferably, the element includes more than one the arm.

Preferably, the base further includes at least one aperture shaped to receive a corresponding at least one the arm.

Preferably, the base and the arms are formed from a single piece of material.

Preferably, the base and the arms are formed separately and the arms are pivotally connected to the base and biased to a position away from the base.

Preferably, the material is a sheet material and the arms are bent back on the base.

Preferably, the apertures are shaped to retain respective wire engaging portions after being received.

Preferably, the element further comprises a terminal portion depending from the base.

In a further aspect, the invention comprises a medical tube connector comprising a tubular body having a longitudinal axis. A collar extends from the body part way along the body and defines an annular gap between an outer surface and an inner surface of the collar. The annular gap is adapted to receive a tube fitted over the body and under the collar and is adapted to form a substantial seal. The collar further comprises at least one open ended pocket adapted to receive an insulation displacement type element in a direction substantially parallel with the axis of the body.

Preferably, the collar further comprises retaining features for retaining a medical tube.

Preferably, the body is substantially straight.

Preferably, the body is an 'elbow'.

Preferably, the body includes at least one port adapted for receiving a sensor.

Preferably, at least one the pocket is open on each end.

In a further aspect, the invention comprises a retaining collar comprising a plurality of semi-annular segments joined in series via living hinges.

Preferably, one or more of the segments includes a retaining feature on an external surface.

Preferably, one or more of the segments includes a retaining feature on an internal surface.

Preferably, one or more of the segments includes an open ended pocket adapted to receive an insulation displacement element.

In a further aspect, the invention comprises a method of terminating a medical tube comprising taking a medical tube and winding at least one insulated wire around an outer surface from at least substantially one end to the other, capturing the wire so that it is substantially stationary with respect to the tube, and pushing at least one insulation displacement element over the wire to complete an electrical connection.

Preferably, the tube includes a recess in the outer wall and the insulation displacement element is located at least partially in the recess after installation.

Preferably, the tube includes more than one insulated wire wound around an outer surface from at least substantially one end to the other.

Preferably, the insulation displacement element is engaged over at least two insulated wires to electrically connect parts of an electrical circuit.

Preferably, the insulation displacement element is located entirely in the recess after installation.

Preferably, the step of capturing the wire includes fitting a retaining collar over an end of the conduit.

Preferably, the collar is the collar of any one or more of claims 7.1 to 7.4.

Preferably, the step of capturing the wire includes fitting an end connector over an end of the conduit.

Preferably, the method includes pushing more than one insulation displacement element over the wire to join parts of an electrical circuit.

Preferably, the insulation displacement element is as claimed in any one or more of claims 3.1 to 5.8.

Preferably, the end connector is as claimed in any one or more of claims 6.1 to 6.6.

Preferably, the method further includes fitting a sheath over the outer surface of the tube and over the wire.

Preferably, the medical tube is as claimed in any one or more of claims 1.1 to 2.7.

Preferably, a wire support member is fitted to the tube to support the wire before the step of pushing the insulation displacement element over the wire.

Preferably, the wire support element comprises a ring shaped body having at least one wire support finger extending parallel with an axis of the ring body and the wire support finger is located in the recess such that the wire support finger is between an outer surface of the tube and the wire and supports the wire in the recess away from the tube.

Preferably, the insulation displacement element is fitted over the wire support finger when engaging the wire.

Preferably, the wire support member includes a plurality of wire support fingers extending parallel with an axis of the ring body and spaced around the perimeter of the member.

Preferably, the tube includes a plurality of the recesses and each of the plurality of wire support fingers is located in a respective recess.

Preferably, there is an insulation displacement element in each recess and fitted over a respective the wire support finger.

In a further aspect, the invention comprises a method of terminating a medical tube substantially as herein described and with reference to any one or more of the drawings.

In a further aspect, the invention comprises a method of terminating a medical tube substantially as herein described and using any one or more of the components claimed in any one of the preceding claims.

In a further aspect, the invention comprises a method of forming a medical tube substantially as herein described and with reference to any one or more of the drawings.

In a further aspect, the invention comprises a method of assembling a medical tube substantially as herein described and using any one or more of the components claimed in any one of the preceding claims.

In a further aspect, the invention comprises a medical tube assembly substantially as herein described and with reference to any one or more of the drawings In a further aspect, the invention comprises a medical tube assembly substantially as herein described and using any one or more of the components claimed in any one of the preceding claims.

BRIEF DESCRIPTION OF THE DRAWINGS

FIG. 10b is a bottom view and cross-section detail of an end of the medical conduit of FIG. 10a.

FIG. 17 is an end cross section view of the connector assembly of FIG. 16a.

DETAILED DESCRIPTION OF THE PREFERRED EMBODIMENT

In this specification, terms "medical circuit" and "breathing circuit" are used to indicate the general field of the invention. It is to be understood that a "circuit" is intended to include open circuits, which do not form a complete closed circuit. For example, CPAP systems typically consist of a single inspiratory breathing tube between the blower and the patient interface. The term "breathing circuit" is intended to include such "open circuits". Similarly, the term "medical circuit" is intended to include both breathing circuits and insufflation circuits (which are also typically "open"). Similarly, the term "medical tubing" is intended to be read as flexible tubing suitable for use in the type of medical circuits described above connecting between components of a medical circuit and providing a low resistance gases pathway between components of a medical circuit.

Figure 1:
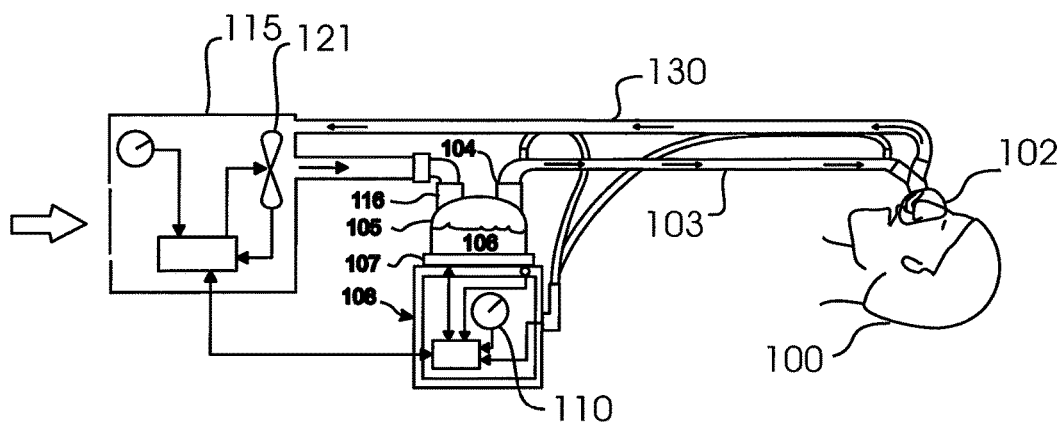
FIG. 1 is a schematic illustration of one type of breathing circuit in which a component according to the invention may be used.

In the field of medical circuits, and in particular breathing circuits (including anaesthetic circuits), condensation or rain-out can be a particular problem where high humidity breathing gases come into contact with the walls of a component at a relatively lower temperature. With reference to FIG. 1 a humidified ventilation system is shown in which a patient 100 is receiving humidified and pressurised gases through a patient interface 102 connected to a humidified gases transportation pathway or inspiratory breathing tube 103. It will be appreciated the patient interface 102 may take the form of a nasal mask, oral mask, oronasal mask, nasal prongs, endotracheal tube or full-face mask, etc.

It should be understood that delivery systems could also be continuous, variable or bi-level positive airway pressure or numerous other forms of respiratory therapy. The inspiratory tube 103 is connected to the outlet 104 of a humidification chamber 105 which contains a volume of water 106. The inspiratory tube 103 may include a heater or heater wires (not shown) which heat the humidified gases within the tube to reduce the formation of condensation. The humidification chamber 105 is heated by a heater plate 107 of humidifier base 108. The humidifier 108 is provided with an electronic controller which may comprise a microprocessor based controller executing computer software commands stored in associated memory.

In response to the user set humidity or temperature value input via dial 110, for example, and/or other inputs, the controller determines when (or to what level) to energise heater plate 107 to heat the water 106 within humidification chamber 105. As the volume of water is heated, water vapour begins to fill the chamber above the water's surface and is passed out of the humidification chamber outlet 104. A flow of gases (for example air) is provided from a gases supply or ventilator 115 which enters the chamber 105 through inlet 116. Exhaled gases from the patient's mouth are returned to the ventilator via a return expiratory breathing tube 130, that may also include a heater or heater wires (not shown) which heat the humidified gases within the expiratory breathing tube to reduce the formation of condensation.

It is preferable that medical tubing (for example the inspiratory and/or expiratory breathing tubes 103, 130) is: resistant to crushing, resistant to restrictions in flow when bent (increased resistance to flow <50% when bent around a 1 inch cylinder), resistant to kinking, resistant to changes in length/volume under fluctuating internal pressure (compliance), resistant to leaking (<25 ml/min @6 kPa), has low flow resistance (increase in pressure @ max. rated flow <0.2 kPa), electrically safe i.e. sparks in the tubing can be extremely dangerous, especially in oxygen-rich environments such as oxygen therapy, and of single lumen design.

International standard ISO 5367:2000(E) (Fourth edition, 2000-06-01) is one example of how some of these desirable parameters are measured and quantified, and the document is hereby incorporated into this specification in its entirety by reference. It is preferable that components of the invention meet or exceed some or all of these standards.

In alternative embodiments, components meet all of these standards.

Breathing Tube

Helically wound medical tubing including helical reinforcing bead(s) have been previously provided to improve crush resistance and to prevent blocking while maintaining a flexibility enabling the medical tubing component to bend easily without kinking. The helical nature of the reinforcing bead lends itself to the winding of an external heater wire around the tube. However, these types of conduits are relatively difficult and slow to manufacture, resulting in higher costs. In many medical applications, breathing tube components are "single use" and are discarded regularly. Therefore, cost is a very important consideration for producing commercially viable products.

However, the present invention can be applied to medical tubing formed in this way. Alternatively, other known methods suitable for forming tubing with helical wire winding pathways, are suitable for the present invention.

Particularly for single use breathing tubes, a substantially uniform wall thickness extruded and corrugated tube is significantly cheaper and faster to manufacture and has therefore typically been preferred (for example breathing tubes formed from an extruded tubular parison). Preferred embodiments of heated medical tubing are described in detail in U.S. patent application No. 61/357,333, the entire contents of which is herein incorporated by reference.

Figure 2A:
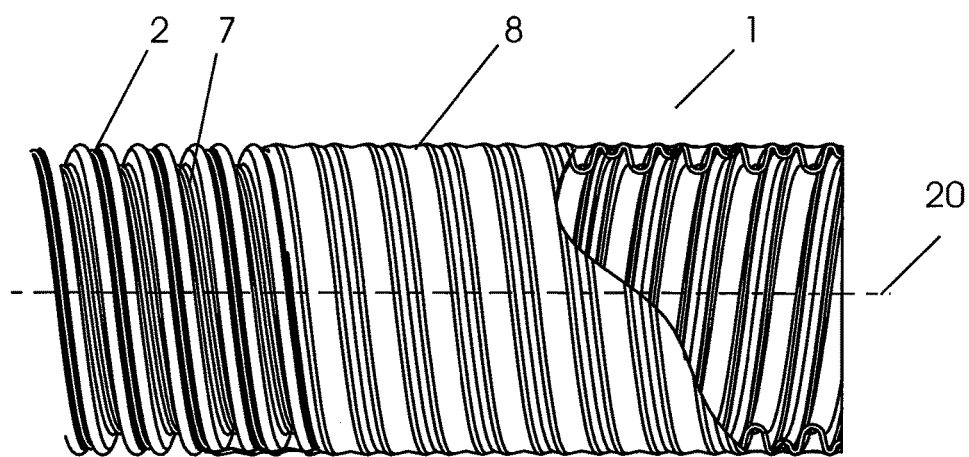
FIG. 2a is a partial cut-away side view of a medical tube component according to one embodiment of the invention.
Figure 2B:
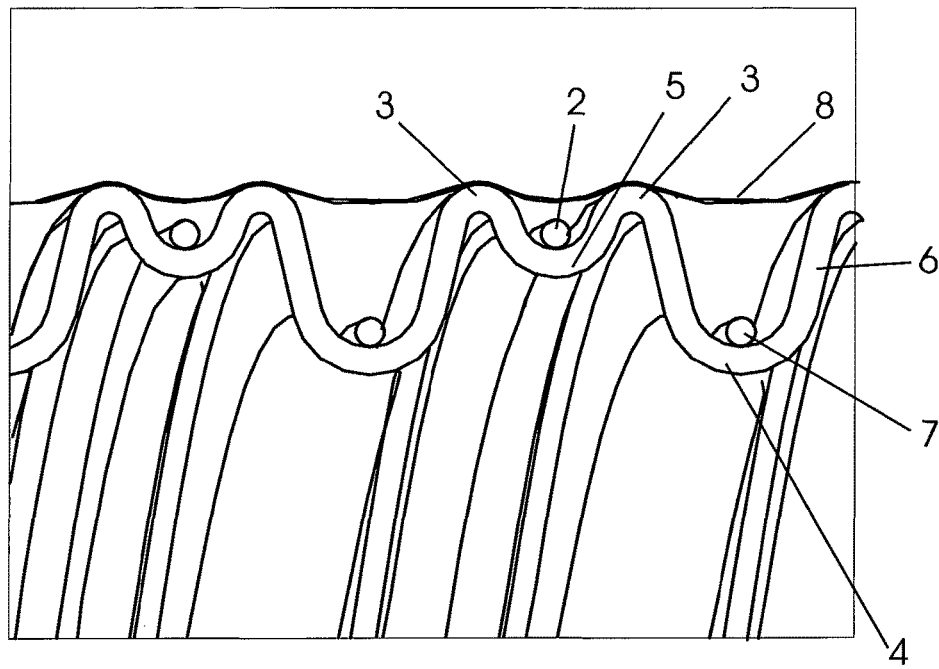
FIG. 2b is a cross section view of the component of FIG. 2a showing a preferred corrugation profile.
Figure 3:
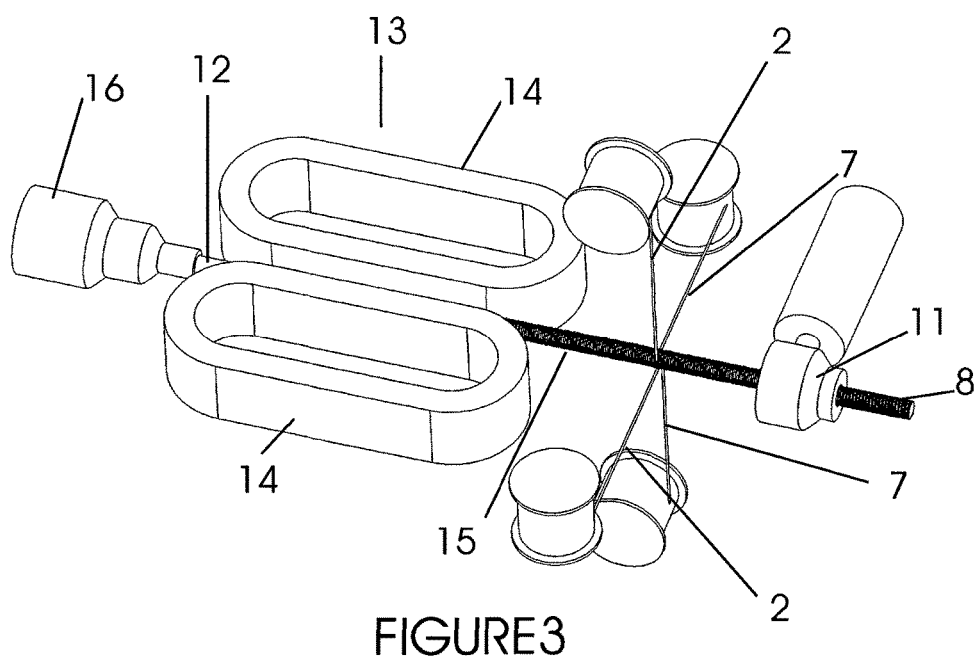
FIG. 3 is a schematic illustration of a preferred forming method for medical tubing.

With reference to FIG. 3, the preferred process for making medical tubing involves extruding a molten tubular profile 12 into a corrugator machine 13 utilising an endless chain of mould blocks 14 to form a flexible helically corrugated tube 15. An extruder 16 equipped with a 30-40 mm diameter screw and a 12-16 mm annular die head with gap of 0.5-1.0 mm has been found to be suitable for producing low cost tubes quickly. During manufacture, the molten tube 12 is passed between a series of rotating moulds/blocks 14 on the corrugator after exiting the extruder die head 16 and is formed into a corrugated tube such as that illustrated in FIG. 2 for example. The molten tube is formed by vacuum applied to the outside of the tube via slots and channels through the blocks and/or pressure applied internally to the tube via an air channel through the centre of the extruder die core pin. If internal pressure is applied, a specially shaped long internal rod extending from the die core pin and fitting closely with the inside of the corrugations may be required to prevent air pressure escaping endways along the tube.

The medical tubing has a wall that is preferably between approximately 0.3-1 mm thick for a breathing tube of typical dimensions (i.e. between approximately 10 mm and 35 mm diameter for neonatal and adult applications respectively and approximately 1-2 meters in length).

With reference to FIGS. 2a & b, one preferred embodiment will now be described in detail although the present invention also finds application in corrugated tubes with more conventional corrugation shapes.

Breathing tube 1 with corrugations formed in a helical manner is shown. The corrugations comprise a series of alternating outer crests 3 and inner troughs 4 with respect to centre line 20. At the peak of each outer crest 3, is a local trough 5 comprising a small (with respect to the amplitude of the corrugations) inward dip in the peak. As a result, the outer crest 3 is intended to denote a region comprising the local trough 5 and the two local peaks adjacent either side.

An electrical heating wire 2 is placed in direct external contact to the tube 1, and wound along the local trough 5 associated with the outer crests 3 of the helical corrugations. Because the heater wire is associated with the exterior surface of the breathing tube, the gases flow through the conduit is not further disturbed by the presence of a heater wire in the flow path. The heater wire 2, is preferably of a small diameter compared to the diameter of the tube, for example less than ⅕th. The angle of the spiral will affect the overall flexibility of the tube once the heater wire(s) are wound around the tube.

It is necessary for the tube to be able to bend and stretch without breaking the heater wires. This is achieved by making the spiral angle high (i.e. the heater wire wraps around the circumference more per unit length) and avoiding configuration in which the heater wires are nearly aligned with the longitudinal axis of the tube.

According to further preferred embodiments, a thin external sheath 8 (shown in FIG. 2) may be added to cover the heater wires 2, 7 to prevent them being dislodged and to further prevent heat loss. The sheath 8 provides an insulating barrier by trapping air in the space between the corrugations.

The sheath 8 may or may not contact and hold the heater wire in place. The sheath can be formed by for example; spiral wrapping a cling tape over the outside or by feeding the mandrel through a cross-head die 11 and extruding a thin flexible plastic sheath 8 over the top as shown in FIG. 3. The sheath has the added benefit of improving compliance, pull strength, resistance to flow with bending and crush resistance, although it is important that the overall product still remains flexible to ensure adequate patient comfort etc. It will be appreciated that if an extruded sheath is employed, it may be able to be bonded securely to the tube during the extrusion process. This may have benefits in improving the torsional resistance of the tube and limit the effects of a torsional "worming" action that can occur with a spiral formed tube during pressure pulses as typically experienced in a breathing circuit.

The sheath 8, may be of the same material (or same base material) as the breathing tube, particularly for embodiments where bonding between the sheath and tube or between the sheath and breathing tube end connectors is desired. Bonding, if any, may be from residual heat in the sheath as it is formed over the breathing tube, and/or auxiliary heating or welding or adhesive processes may be employed. Alternatively, the sheath 8 may be of a different material, and a bonding agent may be applied if bonding is desired.

It will be appreciated that other reinforcing processes may still be used supplement the tube in order to improve its performance characteristics still further (such as compliance, pull strength, resistance to flow with bending and crush resistance). Those processes may or may not be integrated with the tube forming process.

It is preferable that the heater wire 2 is formed in an electrical loop so that the electrical circuit starts and finishes at the same end of the breathing tube 1, which can be attached to a medical respiratory device that provides power to the heater wire circuit. Therefore a second strand of heater wire 7, is preferably provided in the inner trough 4. The second strand of heater wire 7, is subsequently joined to heater wire 2 after winding to complete the electrical circuit.

It can be seen in FIG. 2a that the corrugations are helical. This allows the heater wire strands to be continuously wound around the tube. In the embodiment illustrated, the tube has the form of a double helix, with one helix following the crest corrugation and the other following the trough corrugation.

In other alternative embodiments, other multiple helix corrugations may be employed. Alternatively, the heater wire path may not take the "crest & trough" form (having a heater wire associated with the crest), but may take a simpler form where each wire follows a trough helix. In these embodiments the tube may also take a multiple helix from to accommodate 2 or more heater wire "runs" along the length of the tube.

In another alternative embodiment, the outer surface of the main part of the tube length may include corrugations that are semi-annular. This is, for the most part the corrugations may be substantially annular, and include a transition region for the wire winding path to cross over to neighbouring semi-annular corrugations. A similar "semi-annular" arrangement is illustrated in a region of the embodiment illustrated in FIG. 4 and described in detail with reference to the cuff region later.

With reference to FIG. 3, rotating mould blocks 14 are arranged in an endless chain. The endless chain contains mould blocks corresponding to two full lengths of medical tubing in a continuous loop. The rotating mould blocks 14 corresponding to the end portions of each length of tube include end cuff features that are formed at the same time as the tubing.

Figure 4A:
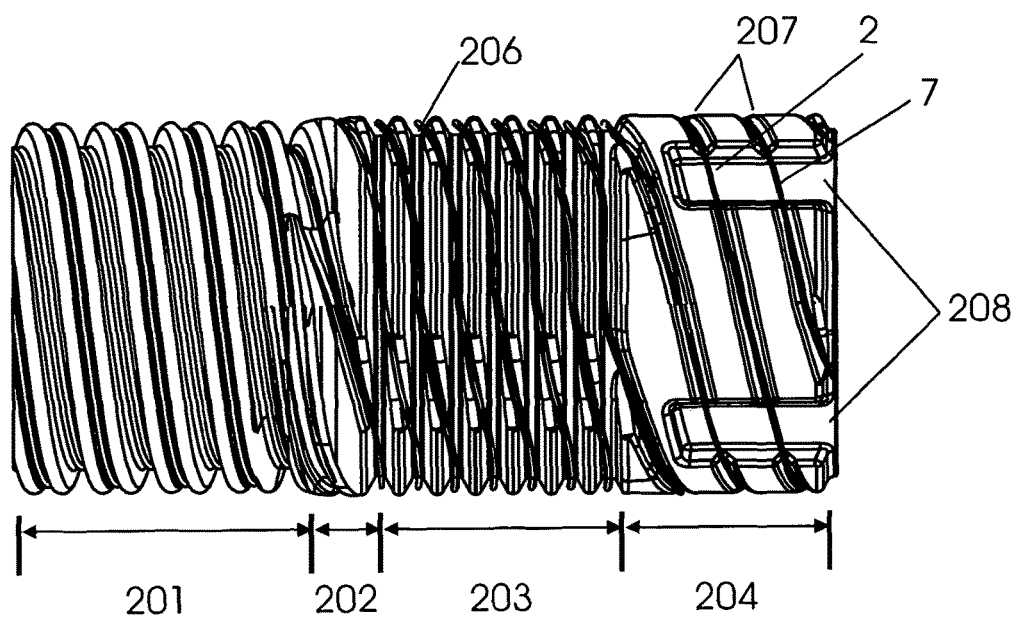
FIG. 4a is a side view of a medical conduit showing one preferred corrugation transition and termination region.
Figure 5:
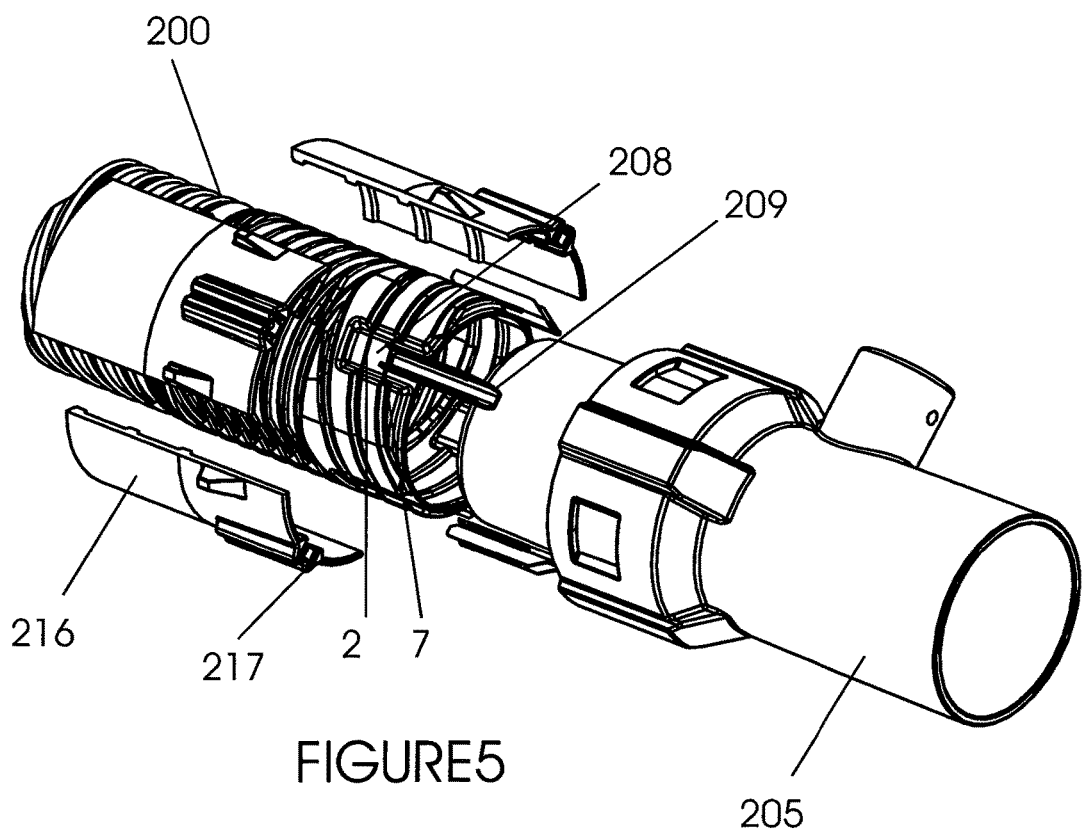
FIG. 5 is an exploded view of medical tubing and end connector assembly showing the preferred corrugation transition and termination regions.

With reference to FIG. 4*a*, the end cuff region (202+203+204) of medical tubing 200 is formed at the same time as the spiral/helical corrugations (region 201), and is configured to receive an end connector fitting 205 (shown in FIG. 5). To facilitate the connection and heater wire routing between the spiral corrugation region 201 of tube 200, and the semi-annular cuff corrugation sealing region 203, a transition region 202 may be provided. The region 202 transitions from the helical corrugation profile to a mostly annular corrugation profile (semi-annular) adjacent the termination portion 204. The annular corrugation region 203 provides an improved seal between the exterior surface of the end connector 205 because the inner surface of each annular corrugation contacts the end connector 205 in substantially sealed rings.

Also the geometry of the corrugations provides a useful increase in sealing pressure and reduces the effects of diametric tolerances because the flexing of the angled walls transfers the hoop loads from the rings over a wide range of interference fits. This also allows the cuff region (202+203+204) to be the same thickness as the helical corrugations of the tubing, thereby maintaining a constant production speed i.e. the endless chain of mould blocks 14 does not need to slow down when forming the cuff region to increase the wall thickness.

Annular corrugation region 203 has angled channels 206 formed in, or on, the annular sealing rings. This allows the heater wires to step over each annular ring as they transition along the cuff region 203. At the end of tube 200 is termination region 204. Region 204 includes helical groves 207 within which heater wires 2, 7 are routed.

Termination portion 204 also comprises a series of termination channels 208, extending parallel to the axis of tube 200 and spaced around the circumference. As shown in FIG. 4*a*, heater wires 2, 7 pass over termination channels 208 and are not in contact with tube 200 in this region. As a result of being offset from the channel 208, access to the wire is improved when inserting the connectors as described in more detail later.

Figure 6:
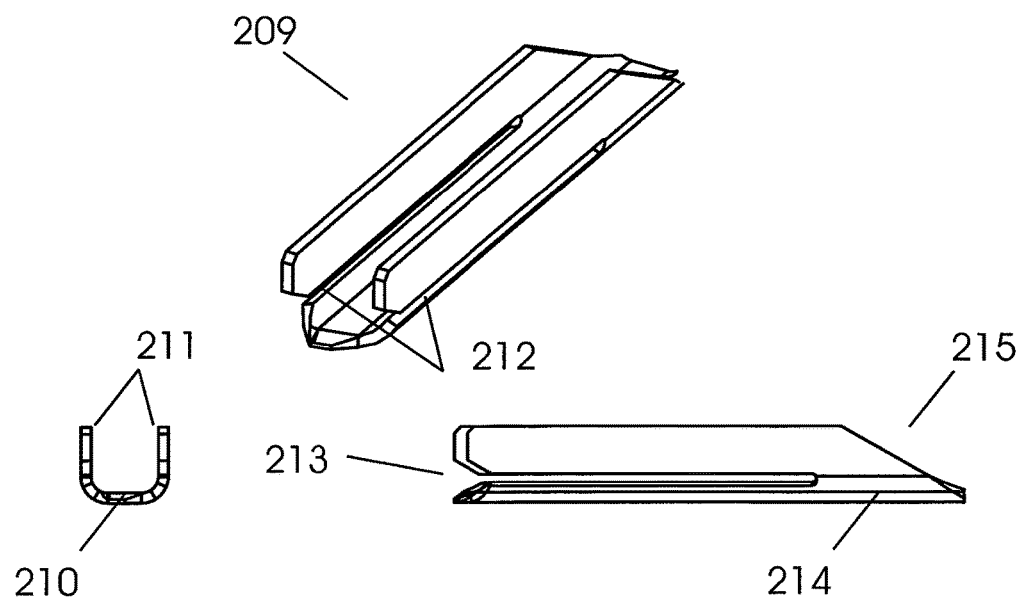
FIG. 6 illustrates one preferred form of an insulation displacement member according to the invention.

In order to complete the electrical circuit between heater wire 2 and heater wire 7, an Insulation Displacement Connector (IDC) is used. With reference to FIG. 6, IDC 209 comprises a substantially U-shaped channel member of an electrically conductive material. The channel member 209 includes base 210 inside parallel side portions 211. Channel member 209 further includes slots 212 separating respective side portions 211 from base 210 along a substantial length of the IDC 209. As a result IDC member 209 has an open end 213 and a closed end 214 where the side portions 211 attach to base 210. Preferably, the open end 213 includes a chamfered mouth region (associated with the base 210 and/or side portions 211), to help guide the wire into slots 212. Closed end 214 may have a chamfered portion 215 as shown in order to mate with correspondingly shaped recess within raised channel features 223 in collar 220 (see FIG. 8).

Figure 4B:
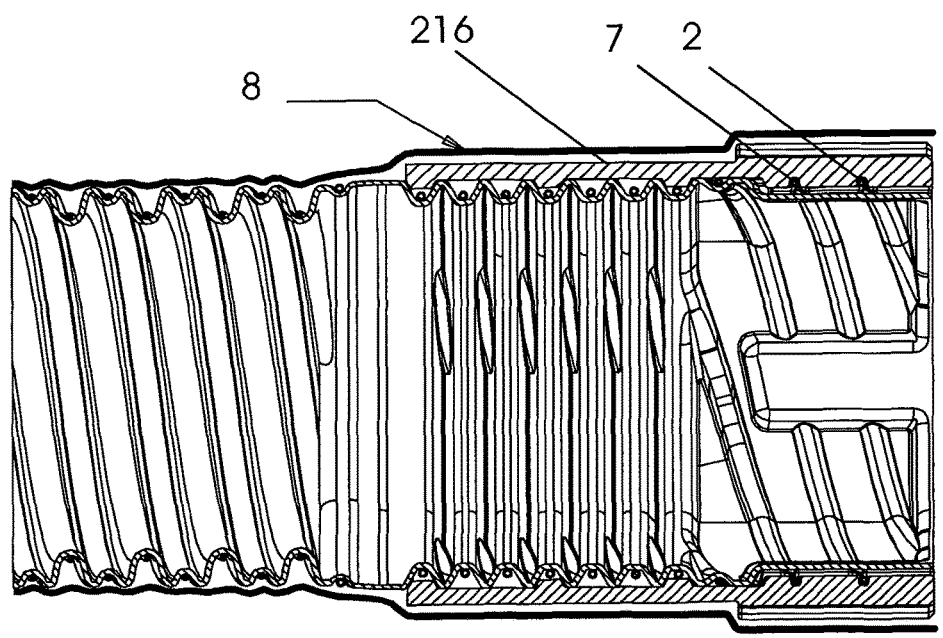
FIG. 4b is a cross section view through an end region of the medical conduit of FIG. 4a including an outer sheath.
Figure 7A:
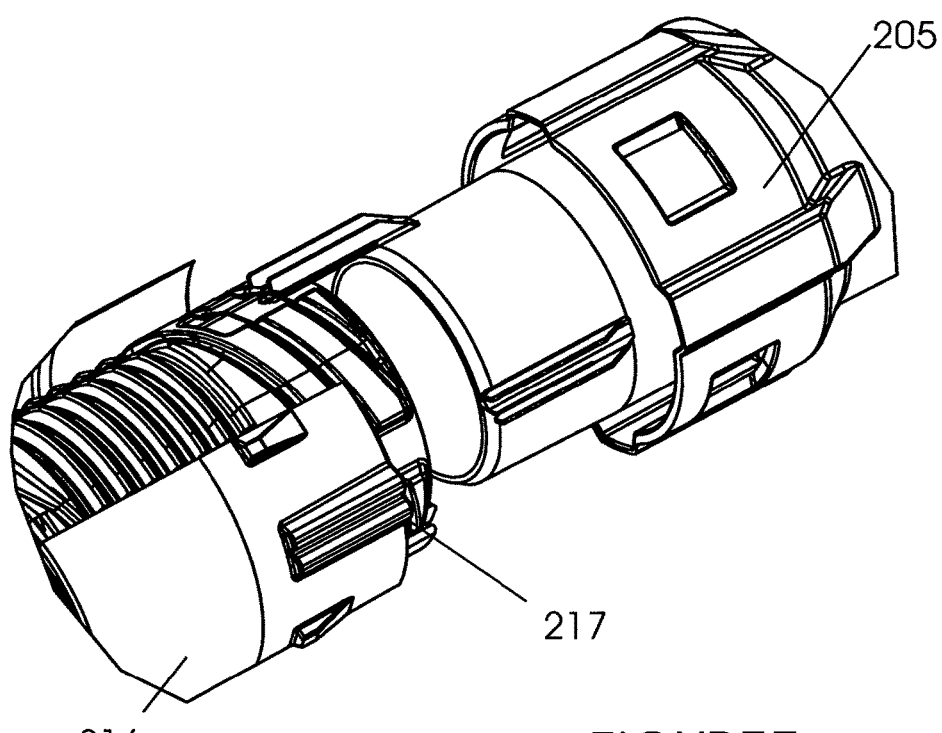
FIG. 7a is a cut-away and exploded view of medical tubing showing the insulation displacement member of FIG. 6 partially inserted.
Figure 7B:
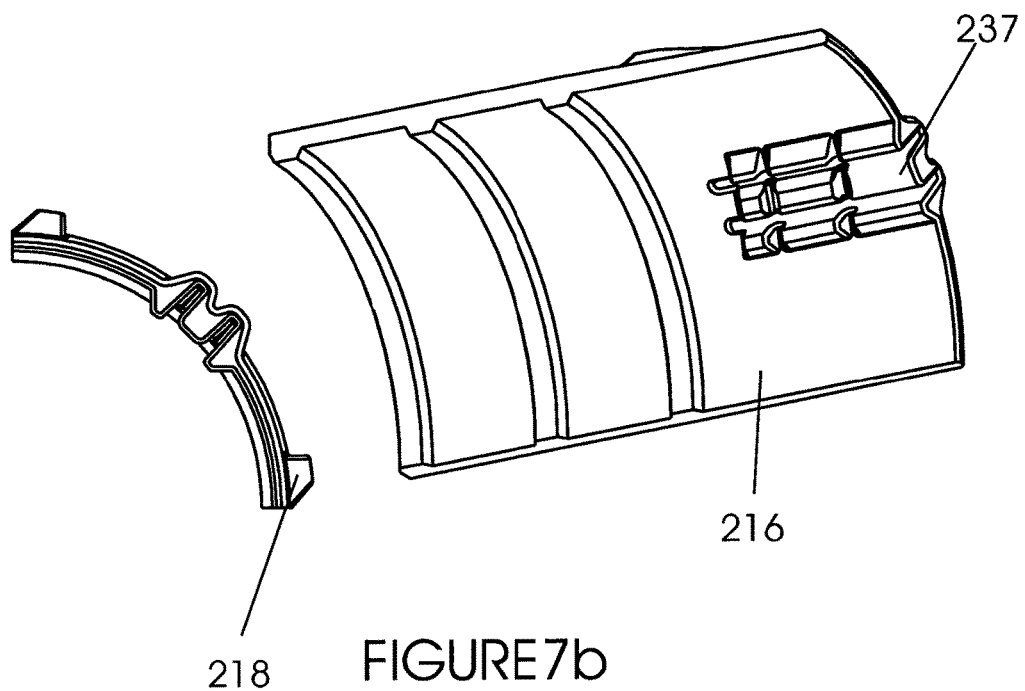
FIG. 7b is a perspective view of the inner surface of a single cuff segment and an end view.
Figure 8:
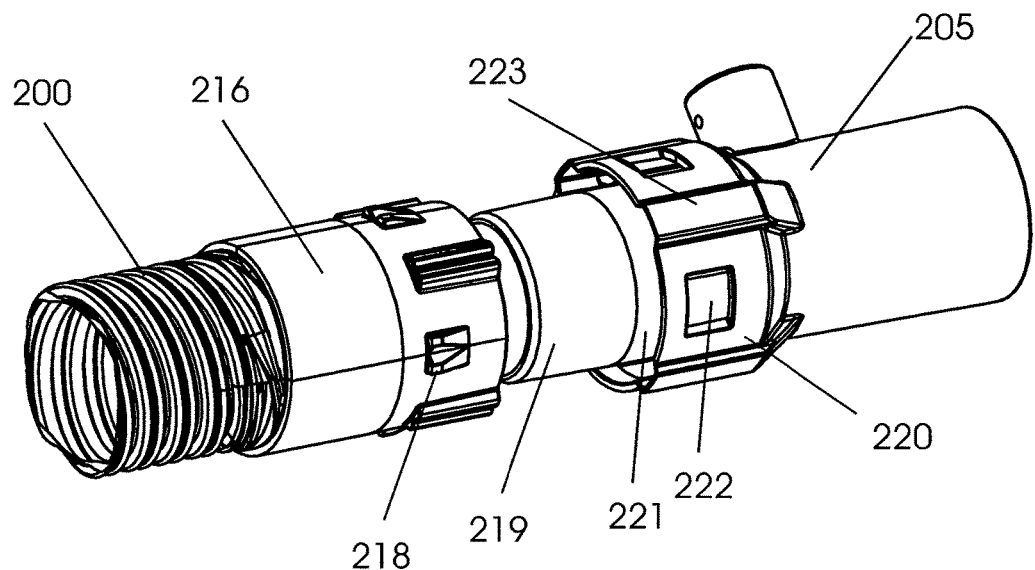
FIG. 8 is a perspective view of a medical tubing assembly according to one embodiment of the invention shown ready to receive an end connector.

With reference to FIG. 4*b* and FIG. 5, the electrical connection between heater wire 2 and heater wire 7 is achieved by first wrapping locating cuff 216 around the end of tube 200. Locating cuff 216 comprises a series of segments (for example 4 as shown) that fit over cuff region 202+203+204, thereby encapsulating and holding the heater wires 2, 7 in place (as shown in FIGS. 4*b*, 7*a* and 8). In one embodiment locating cuff 216 comprises 4 segments joined together to form a strip via living hinges. A single segment is shown in detail 1 in FIG. 7*b*.

Alternatively, the segments may be joined in a strip via other suitable means. For example adjacent edges of neighbouring segments may include complimentary hooks and eyes to hingedly couple them together.

Alternatively, the segments may be single pieces and secured by some other method such as adhesive strips, straps or clamps etc.

Locating cuffs 216 preferably also comprise internal recesses 217 to receive the webs 211 of the IDC 209) on the inner surface of locating cuff 216. The recesses 217 may form corresponding ridges on the outer surface of the cuff segments. Alternatively, the cuff segments may be thick enough to have a smooth outer surface.

When fitting to conduit 200, the recesses 217 align with termination channels 208 to provide a space for an IDC member 209 to be received. Locating cuffs 216 may include features on the inner surface to aid with locating onto the outer surface of tube 200. Locating cuffs 216 also preferably include retaining features 218 adapted to engage with complimentary features on end connector 205 in order to permanently or semi-permanently connect the end connector assembly.

Once the locating cuffs 216 are in place, the tubing then passes into the over-sheath extruder (to apply the sheath 8 if included) and the wire and tubing is subsequently cut to length when the tubes are separated at the cuffs. FIG. 8 illustrates medical tubing 200 with locating cuff 216 fitted around one end. In this embodiment there are 4 IDC members 209 in place electrically connecting 4 separate runs of heater wire 2, 7 which are wound in the troughs and peaks respectively on a double helix tube.

Figure 16A:
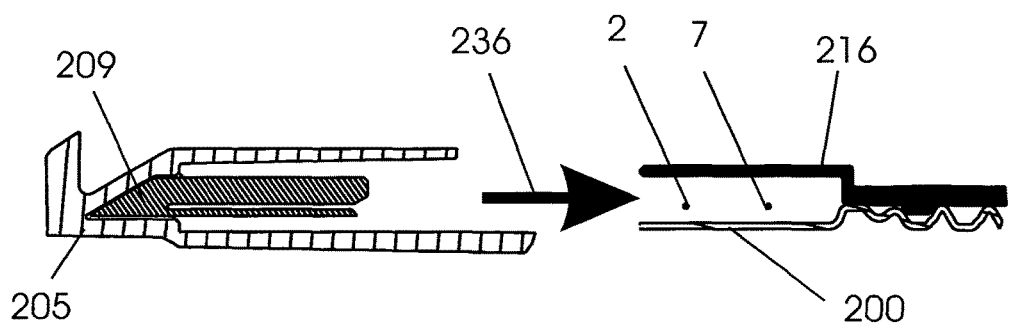
FIG. 16a is a side cross-section (through a web of the IDC) of an end connector assembly shown before fitting to medical tube and cuff.
Figure 16B:
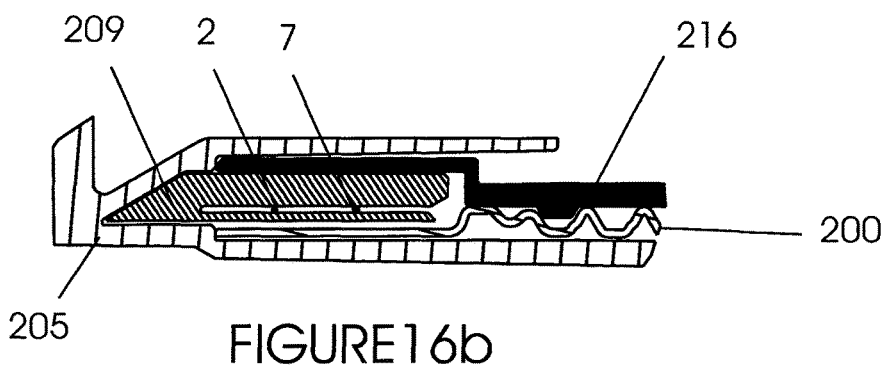
FIG. 16b is a side cross-section view (through the web of the IDC) of an end connector assembly including an IDC, of a preferred embodiment.

After cutting the tube to length, the end connector fitting 205 then has IDC terminals 209 inserted endways into moulded recesses within raised channel 223 in the end connector fitting 205 as shown in FIG. 16*a*. The electrical connection is completed by pushing end connector fitting 205 into the end of tube 200 (in a direction parallel to the longitudinal axis of tube 200 as shown by arrow 236) such that IDC terminals 209 enter into termination channel 208 so that the open end 213 receives heater wire 7. The IDC 209 is pushed far enough such that slots 212 tightly engage both heater wire 7 and heater wire 2 and the heater wire insulation is displaced in the process. FIG. 16 illustrates the assembled configuration of the end connector 205, tube 200, cuff 216 and IDC 209.

Figure 11A:
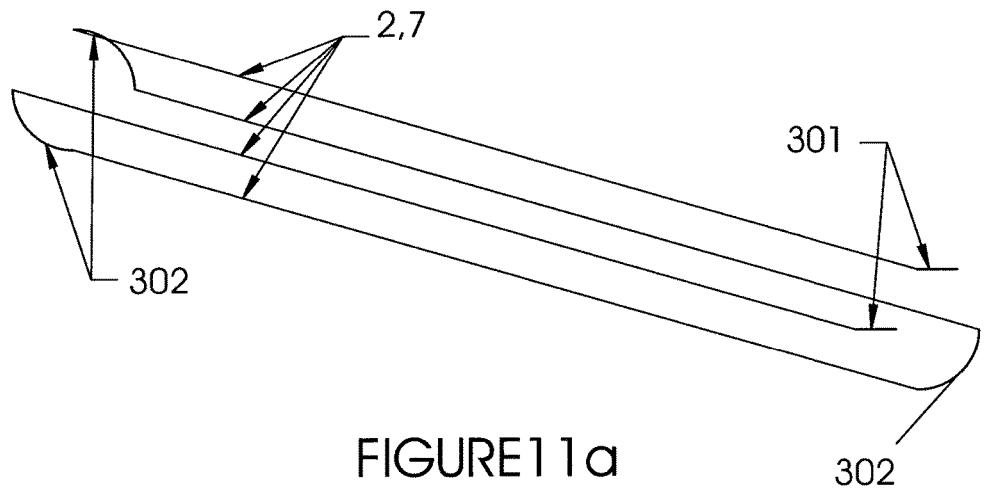
FIGS. 11a-e are schematic wiring diagrams showing alternative placements of IDC connectors on a 4 run medical tube.
Figure 11B:
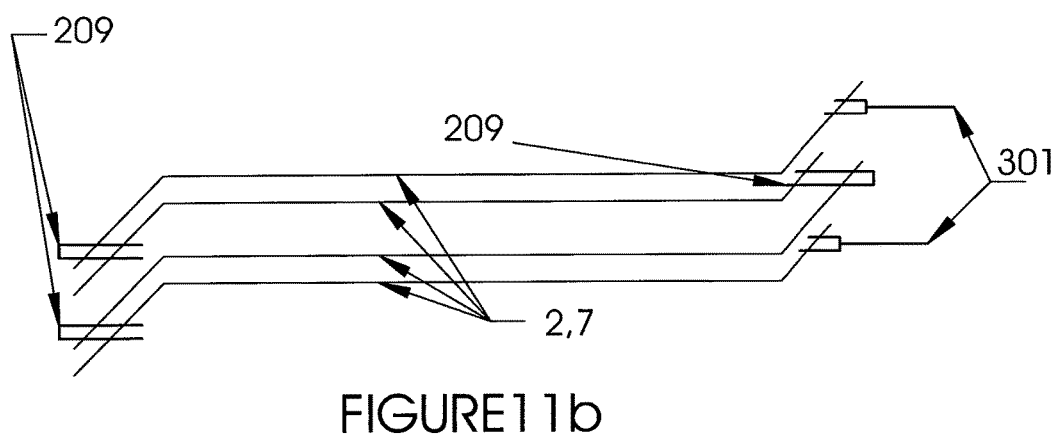

The illustrations of the end fittings in FIGS. 4 to 9 and 13 to 14 (and the tubing 200) can apply to either series or parallel terminations. The difference is the number and arrangement of IDCs fitted. For example in the case of a tube with four runs of wire:

A series circuit as illustrated in FIG. 11*b* having 2 IDC connectors 209 at the patient end and 1 IDC 209 and at the terminal end. In addition, 2 IDC type terminal pins 301 are provided at the machine end.

Figure 11C:
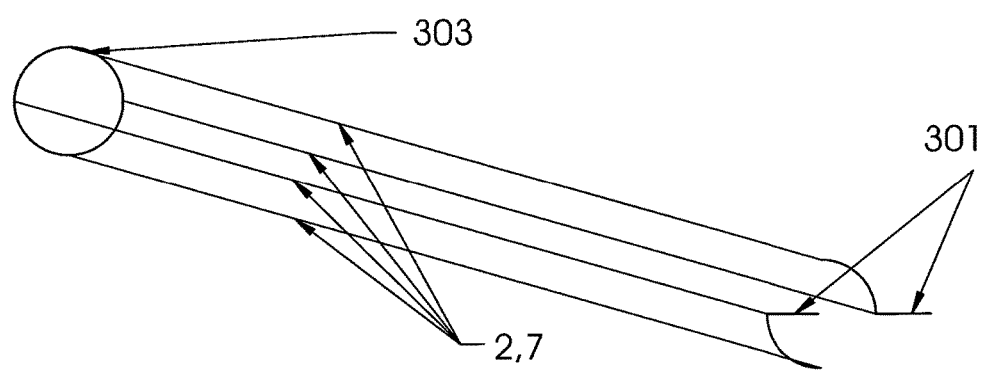
Figure 11D:
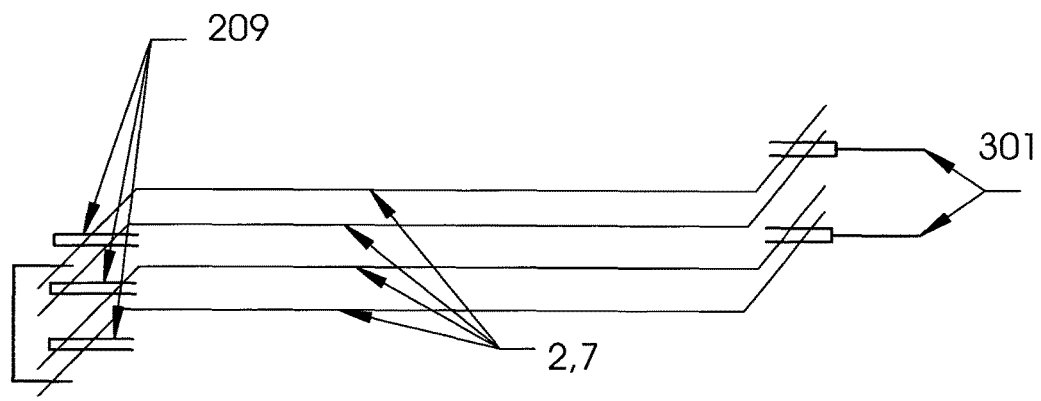

A parallel-series circuit as illustrated in FIG. 11*d* having a 3 (or alternatively 4) IDC connectors 209 at the patient end and 2 IDC connectors 301 (with terminals) at the terminal end.

Figure 9:
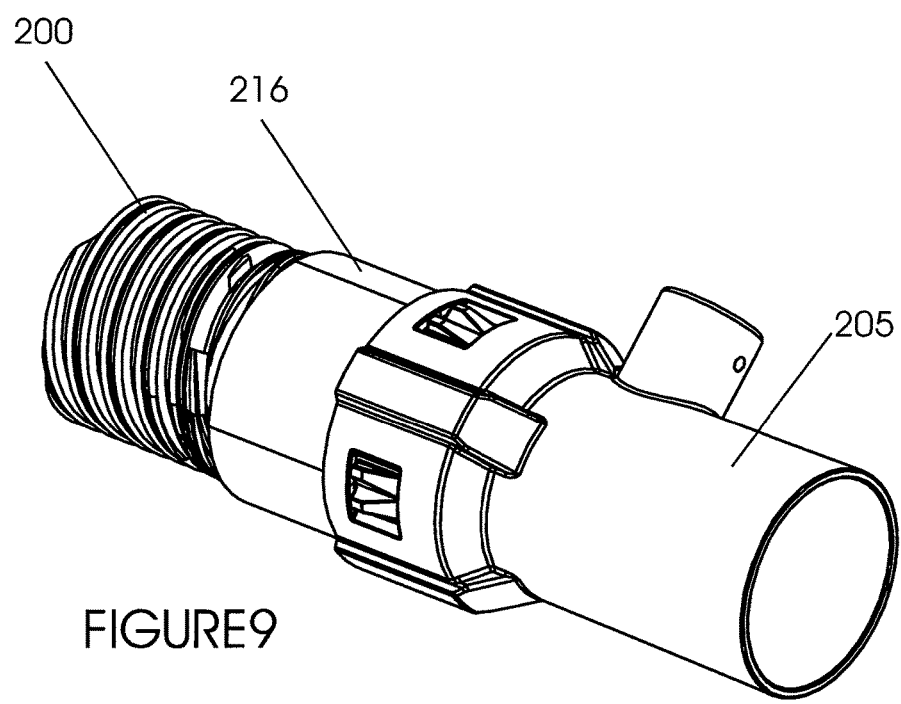
FIG. 9 is a perspective view of the complete end connector assembly of the medical tubing of FIG. 8.

With particular reference to FIG. 8, end connector 205 includes insertion portion 219 which is inserted with a substantially sealing tight fit into tube 200. End connector 205 further includes collar 220 which forms an annular gap 221 between itself and insertion portion 219. As end connector 205 is engaged with tube assembly (200+216) the tube assembly is received in annular gap 221. When fully inserted, retaining features 218 engage with complimentary retaining features 222 on collar 220. Similarly collar 220 includes recess 223 for receiving rib protrusions covering IDC pockets 217 as illustrated in FIG. 9. Alternatively the end connector assembly may be permanently bonded via welding or gluing methods such as: plastic welding, ultrasonic welding, hot met glue, UV glue or any other suitable adhesive.

Figure 13:
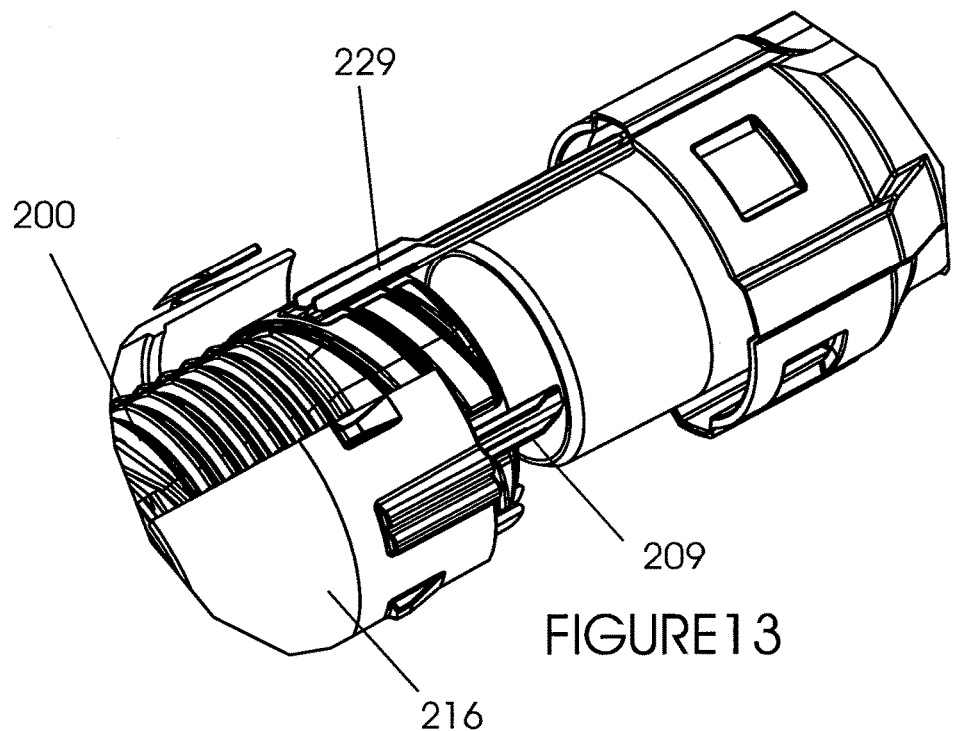
FIG. 13 is a perspective exploded view of a medical tube connector assembly having integrated electrical connectors or a sensor or heater wire plug.
Figure 14:
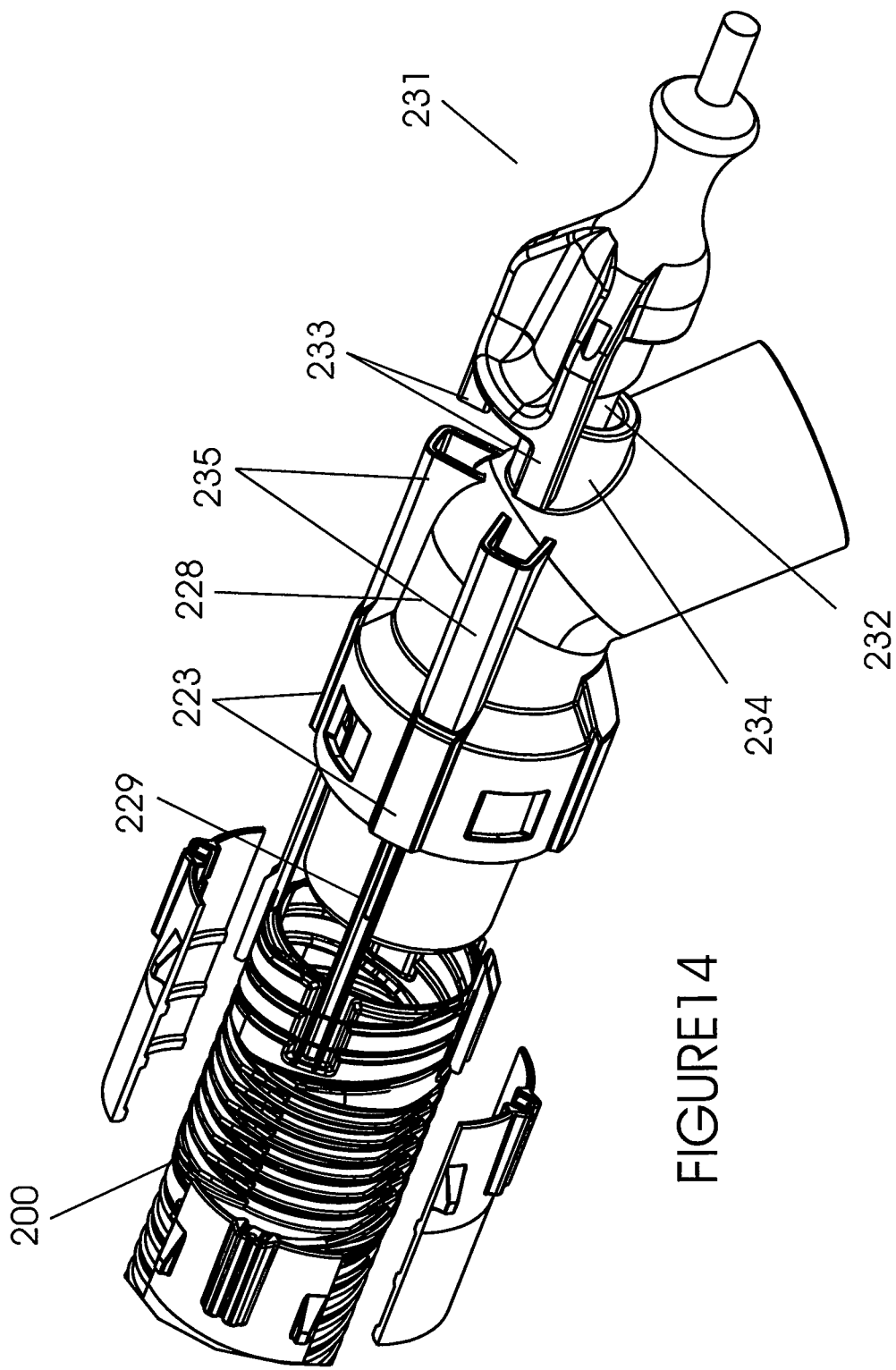
FIG. 14 is a perspective exploded assembly of an end connector assembly according to a further embodiment.

With reference to FIGS. 13-14, an alternative medical tube elbow end connector will be described. The elbow end connector may be particularly suitable for use at the chamber end of a breathing circuit and/or where a sensor is incorporated.

Figure 15:
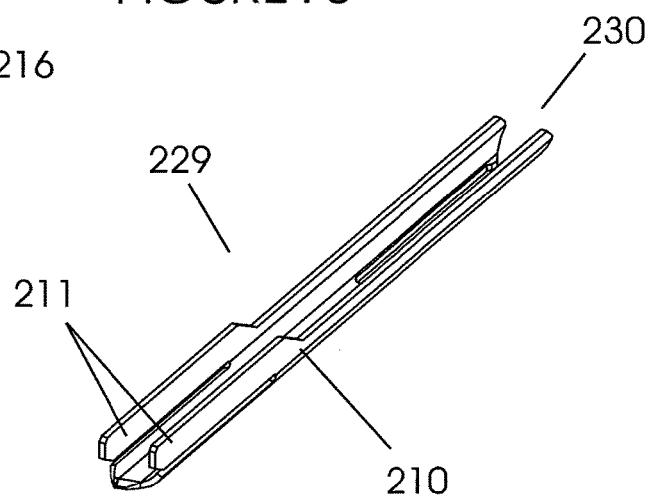
FIG. 15 is a perspective, plan, end and side view of an integrated IDC and plug connector as illustrated in the embodiment of FIGS. 13 and 14.
Figure 15:
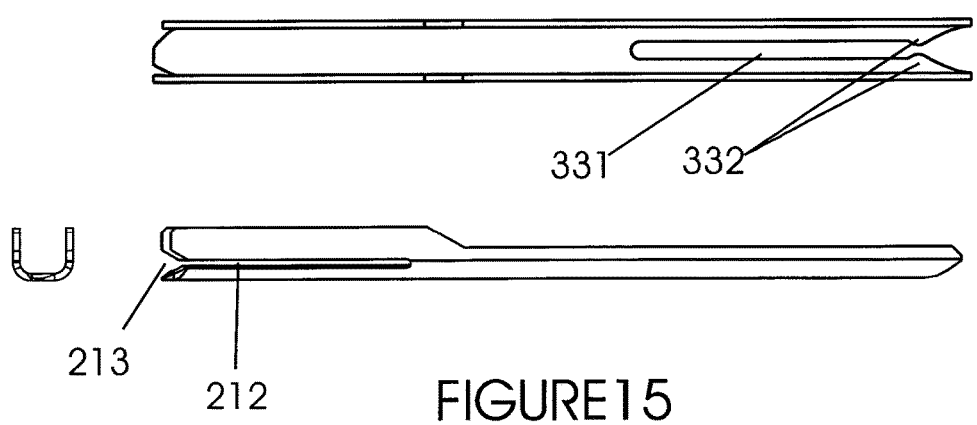

Elbow end connector 228 shares many of the features described with reference to the straight connector 205 with respect to joining onto the tube 200. However the IDC 229 is double ended in that it bridges the wire(s) wrapped around the tube as described earlier, but also provides electrical contacts for the heater plug and/or sensor. With reference to FIG. 15, IDC 229 comprises a substantially U-shaped channel member of an electrically conductive material. The IDC 229 includes base 210, parallel side portions 211. IDC 229 further includes slots 212 separating respective side portions 211 from base 210 along a length of the IDC.

IDC 229 has a first open end 213 and a second end 230. Preferably, the first open end 213 includes a chamfered mouth region (associated with the base 210 and/or side portions 211), to help guide the wire into slots 212. Second end 230 is configured to provide an electrical contact for a heater plug and/or sensor. End 230 preferably includes slot 331 to allow some resilient deformation of the IDC to accommodate a plug and maintain good electrical connection. Further, end 230 preferably includes protrusions 332 to aid positive retention of a correspondingly adapted plug.

In a preferred embodiment illustrated in FIG. 14, heater plug and/or sensor 231 comprises a probe 232 (temperature and/or flow) that projects into the interior flow space of the elbow connector 228 through aperture 234. The elbow connector 228 further includes 223 that allow the second end of IDC 229 to extend into plug sockets 235. Sensor 231 includes plugs 233 configured to slide into sockets 235 and make electrical connection with the second ends of respective IDC's 229. It is preferred that the heater/sensor plug and corresponding end connector socket design facilitate easy alignment and operation and also to prevent reverse electrical connection.

The respective plug and socket connections may take a number of forms. For example, the female socket may be associated with the sensor while the male plug may be associated with the end connector or vice versa. It is also preferred that both socket and plug do not include open contacts, but rather shield the electrical contacts as in the illustrated examples.

Alternative Options

Figure 10A:
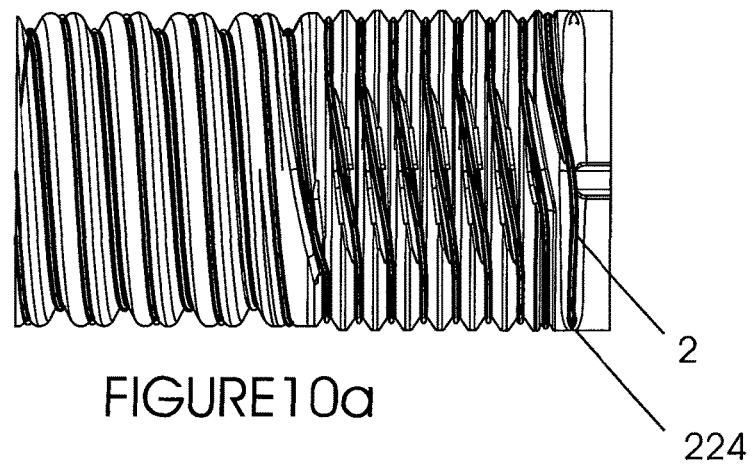
FIG. 10a is a side view of an end of a medical conduit showing a heater wire engaged in a pinch feature.
Figure 10B:
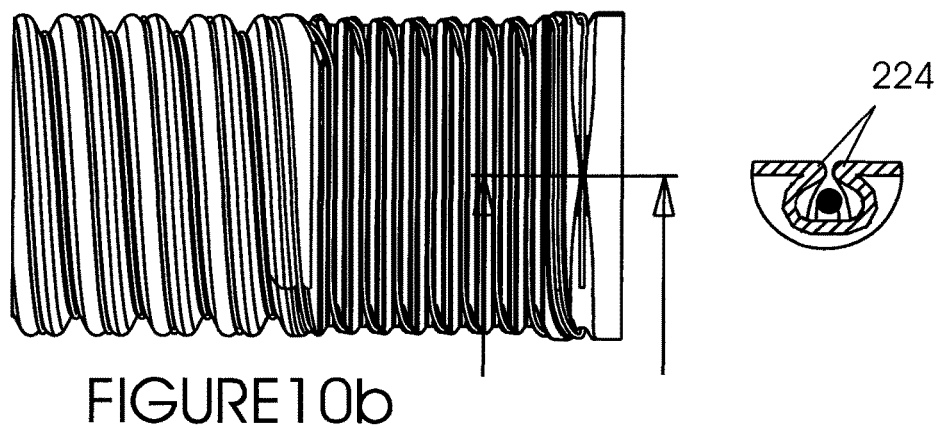

With reference to FIG. 10, further alternative embodiments of the end of the cuff region may also include one or more features to aid in holding the heater wire(s) in place when cutting the tubes to length. FIGS. 10*a* & *b* illustrate the end of the cuff including a pinch feature 224 in which the wire is trapped and pinched.

Figure 10C:
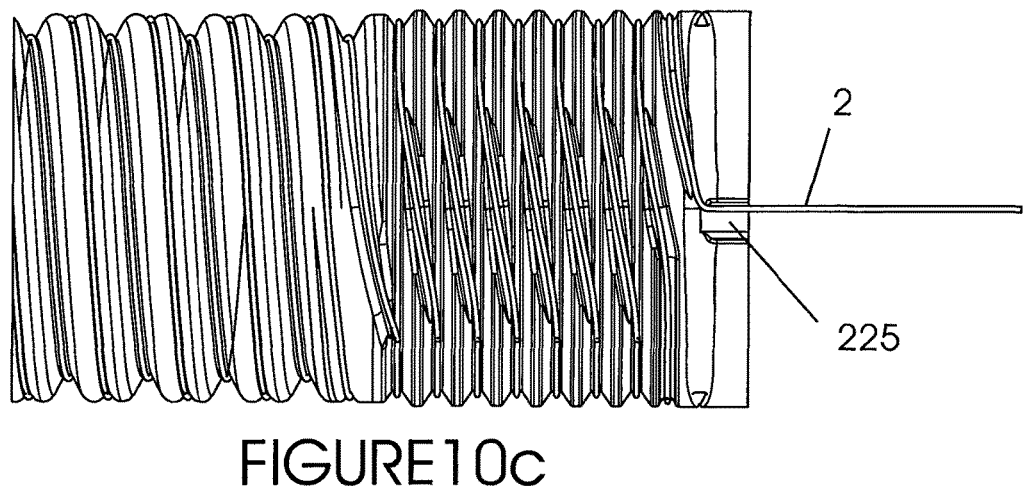
FIG. 10c is a side view of an end of a medical conduit with an end notch.

FIG. 10*c* illustrates the heater wire 2 being withdrawn endways through a cuff end notch 225. The wire is extended in length for terminating operations such as the fitting of terminals etc. This embodiment is particularly helpful where manual termination operations are utilized.

In other preferred embodiments, the heater wire 2 (associated with the outer crest 3) may also be selected with different electrical characteristics to apply a different amount of heat to the crest of the tube, when compared with heater wire 7 (associated with the inner trough 4). For example a higher heating density heater wire (e.g. higher resistance) may be used for the heater wire 2, than the heater wire 7. Alternatively, a lower heating density may be used in the crest wire run.

In a further embodiment, the helical corrugations (either single or multiple helix arrangements) may have a varying pitch along the length of breathing tube. The variation of pitch may be along substantially the entire length (i.e. continuous variation) or may be restricted to different zones along the length. In this way because the heater wires 2, (7 etc) are wound with the corrugation profile, they will also have a varying pitch along the tube length. This results in varying heating density along the tube thereby allowing more or less heat to be applied to different regions of the tube that need it most. For example the chamber end where (typically) the highest rainout occurs (for an inspiratory breathing tube) may have a higher heating density. This is because the gas is typically fully saturated at the chamber outlet. The inspiratory tube is heated to increase the gas temperature along the tube, thereby decreasing the relative humidity (and potential for rainout) of the gas as it flows towards the patient end. Similarly, in an expiratory breathing tube, an increased heating density may be desirable at the patient end of the tube and/or machine end of the tube. Alternatively, the previously described semi-annular embodiments may also be configured to provide a varying pitch along at least parts of the length of the tube.

Figure 11E:
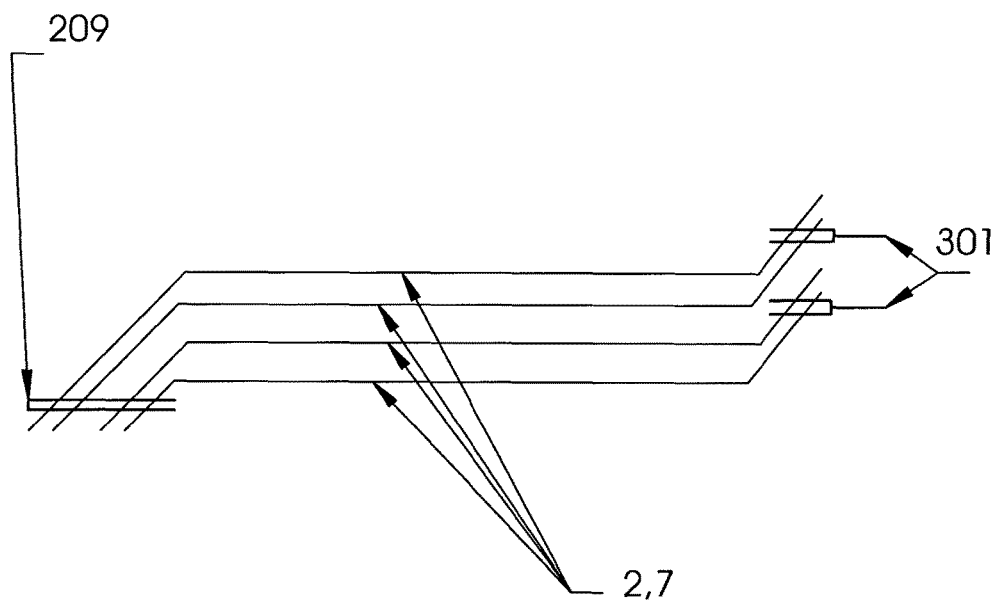

In a further embodiment, the corrugations may be formed in a multiple start arrangement comprising a plurality of helical corrugations (i.e. simply multiple troughs with no crests that can accommodate a heater wire or a double helix incorporating two crests and two troughs per pitch, etc.). With this configuration, as shown in FIG. 3, spiral winding of more than one pair of heater wires 2, 7 can be achieved per revolution. For example, a double helix with heater wire in the crests (only) arranged in an electrical (series) loop. For example, a double helix with heater wire in the troughs (only) arranged in an electrical (series connected) loop. For example, a double helix with a wire in each crest and a wire in each trough (two of each per pitch) arranged in two separate electrical (series connected) loops. This can be achieved by creating two "crest to trough" linked circuits or a "crest to crest" and a "trough to trough" linked circuit. In the case of the latter arrangement, separate electrical control of the heating of crests and troughs would be possible. For example, a double helix with a wire in each crest and a wire in each trough (two of each per pitch) arranged in a single (series connected) electrical loop. This can be achieved by connecting appropriate adjacent crest and trough wire ends to form an arrangement with two return runs (for example the embodiments illustrated schematically in FIGS. 11*a* & 11*b*). For example, a series circuit as illustrated in FIG. 11*a* having 2 arcuate form connectors 302 (90 degrees apart) at the patient end and 1 arcuate form connector 302 at the terminal end. Connector pins 301 are also provided at the terminal end and may be achieved by soldering or crimping or IDC type connections etc. For example, a double helix with a wire in each crest and a wire in each trough (two of each per pitch) arranged in a parallel-series connected electrical loop. This can be achieved by connecting adjacent crest and trough wire ends into two pairs at the chamber end with appropriate terminations such as pins 301 to accept a plug to allow subsequent connection to the power supply. This would form one end of two separate parallel connected pairs. At the patient end, all the wire ends can be linked together in a circumferential loop. This then links the patient ends of the parallel pairs (completing the two parallel loops) and also connects the ends of the two parallel pairs in series to complete the circuit return run (for example the varying embodiments of FIGS. 11*c*, 11*d* & 11*e*). For example, a parallel-series circuit as illustrated in FIG. 11*c* having a ring type connector 303 at the patient end and 2 IDC connectors 301 (with terminals) and at the terminal end. For example, a parallel-series circuit as illustrated in FIG. 11*e* having a 1 multi IDC connector 209 at the patient end (bridging all wire strands) and 2 IDC connectors 301 (with terminals) at the terminal end. For example, a double helix with two wires in tandem in each crest and two wires in tandem in each trough. This would allow multiple combinations of separate or linked circuits connected in series, parallel, parallel-series or series-parallel to provide various winding and termination options for production or to achieve heating or control benefits. Other multiples of helixes per pitch with associated pairs of wires (including tandem wires in each groove) can be employed in a similar fashion with more complex connection options.

The multi-helix arrangement will also reduce the time required to wind the heater wires during manufacture, since the maximum rpm of the winding equipment is limited by balance issues, wire feed speed and safety. Winding multiple wires simultaneously, allows more wire to be wound at any given winding speed. A further benefit arises by increasing the number of breathing tubes (continuous production length) that can be produced before changing reels of heater wire. These benefits directly enhance the throughput of each production line.

The winding process can be performed in a number of ways depending on the desired connection devices and tube handling method(s).

Reverse-Looped Spiral Heating Filament

Figure 12A:
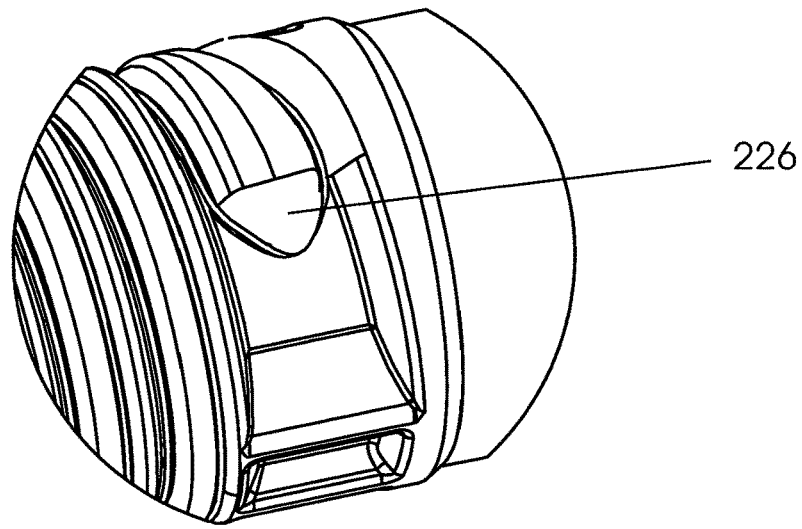
FIG. 12a is a perspective view of a medical tube having a heater wire retaining feature according to one embodiment.

In this embodiment, the wire(s) is (are) wound onto the tube in one direction, and then looped around on the patient end of the tube before winding back along the tube to the starting point to complete the loop. A retaining feature 226 may be included in the tube form to aid the turning of the winding back to the other end (for example as shown in FIG. 12*a*). Tube handling for this method is best performed by cutting the continuous output from the corrugator into individual tubes, loading them onto mandrels and transferring the mandrels onto a winding machine. The winding machine may have several stations that rotate the mandrels and spiral the wire onto the tube, reversing at the end before winding back along the tube to complete the circuit. The loose ends at the chamber end could be retained with a clip system or by hot melt glue or similar adhesive. Once the wire winding is complete, the tube may be optionally sheathed to cover and retain the wire.

Pre-Looped Spiral Heating Filament

In this embodiment, the wire(s) is (are) pre-loaded onto an accumulator system and doubled over complete with a loop in the middle, ready for transfer onto the tube. The wire loop(s) is (are) wound onto the accumulator drum in one direction, then back to the other end. A locator feature 226 (for example as illustrated in FIG. 12*a*) may be provided to secure the wire loop. The winding onto the tube is therefore performed in one direction only. This can either be done on a separate mandrel system as per the previous option or it could be performed in-line direct off the corrugator. The advantages of spiralling on-line eliminate the mandrels and associated handling equipment. Once wire is loaded, the tubing can be routed through a cross-head die for sheathing (if desired) as shown in FIG. 5 for example.

Paired Heating Filaments with Joints at the Patient End

Figure 12B:
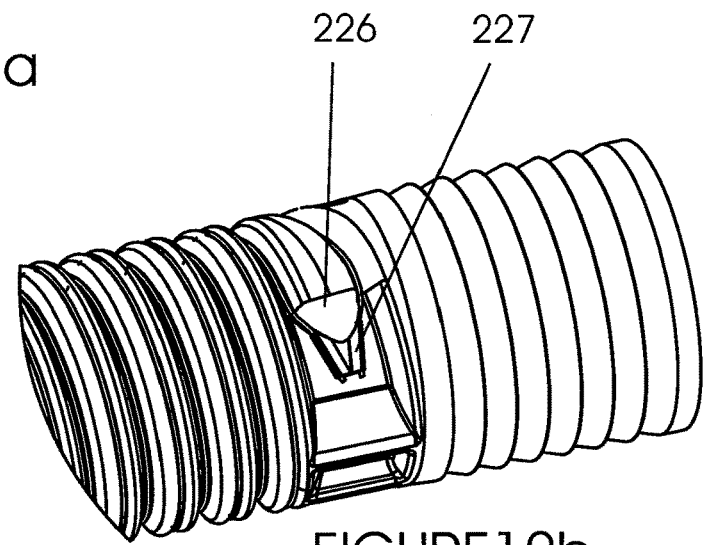
FIG. 12b is a perspective view of a medical tube having a heater wire retaining feature according to a further embodiment.

In this embodiment, corrugated joined tubes pass directly from the corrugator through a joiner/winder assembly. This joins the patient ends of pairs of wire strands together using a crimp 227 and positioned over locating feature 226 as illustrated in FIG. 12*b*. The wires are then positioned over the corrugation spiral and may require further securing with for example, hot melt glue or UV curing adhesive. The retaining feature preferably includes an undercut formation to prevent the wire and/or crimp 227 from disengaging from the retaining feature and coming loose. A winder assembly head then rotates around the tube and applies paired runs of wire from separate spools at the same time. The number of wire pairs to suit the number of helixes per pitch and the desired wire arrangements. The wires may also require securing with for example hot melt glue or UV curing adhesive for example. The over-sheath is subsequently fitted (if desired), and then the tubes are separated at the cuffs. Finally, the cuff fittings and chamber end terminations are fitted.

In an alternative embodiment, the pairs of wires could be continuously spiraled around the tube and joined with a crimp connector without first cutting the wires. The over-sheath is subsequently fitted (if desired), and then the wires are cut after the tubes are separated at the cuffs. Finally, the cuff fittings and chamber end terminations are inserted.

Paired Heating Filaments Continuously Wound On-Line

Figure 12C:
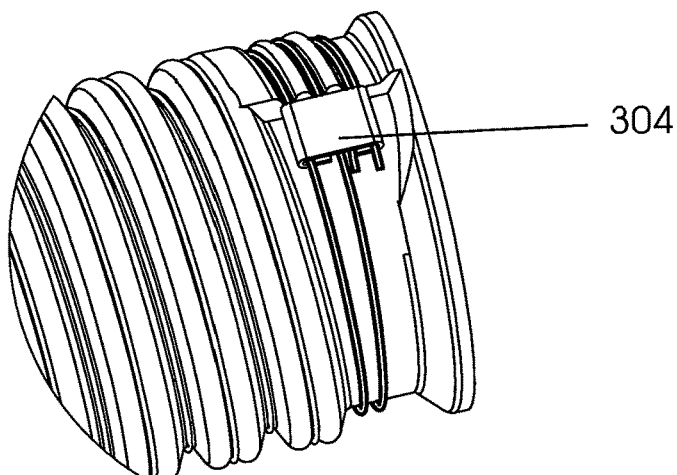
FIG. 12c is a perspective view of a medical tube having a heater wire retaining feature according to yet a further embodiment.

In this embodiment, corrugated joined tubes pass directly from the corrugator through a winder assembly. The winder heads rotate around the tube and apply paired runs of wire from separate spools at the same time. The number of wire pairs to suit the number of helixes per pitch and the desired wire arrangements. The wires may require securing with for example hot melt glue or UV curing adhesive at the ends of the tubing to prevent unraveling once the tubes are separated. This allows for a continuous winding process with the rotational speed of the winding heads largely constant. With reference to FIG. 12*c*, a crimp 304 joins and secures the wires. A retaining feature preferably includes an undercut to prevent the wire and/or crimp from coming loose. The wires are joined with a crimp connector without first cutting the wires. An over-sheath can be subsequently fitted (if desired). The tubes are separated and then the wires are terminated at the chamber end via an appropriate method in a final assembly operation. Feed rate can vary as required to suit the pitch of the grooves at the section of the tube being wound.

In further embodiments it is envisaged that the helical corrugations may also carry conductor(s) for sensing devices located somewhere along the tube i.e. temperature, humidity, flow or pressure sensors. These conductors may share a local trough 5 (and/or inner trough 4) in common with a heating wire or may be formed as an additional helix run. For example, with a separate local trough 5 (and/or inner trough 4). This would remove the need for a user to install a separate external sensing device (such as a temperature probe, humidity sensor or flow sensor) and the associated cable thereby reducing complexity of setup and associated clutter around the patient. Alternatively, the sensor signal may travel over the heater wire(s) itself.

Figure 18:
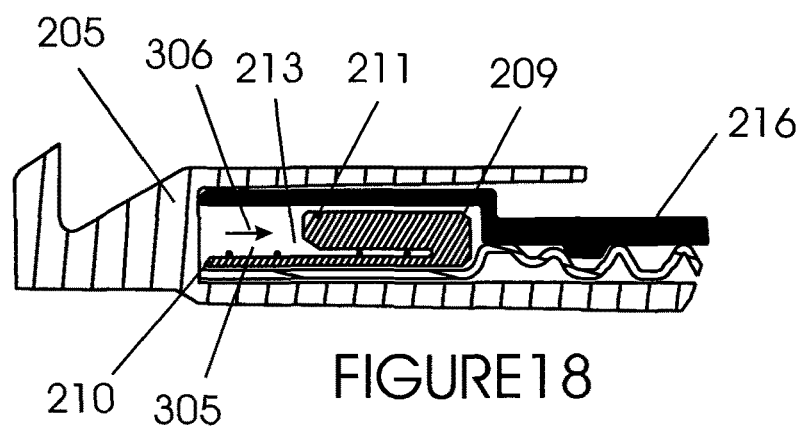
FIG. 18 is a side cross-section view (through the web of the IDC) of an end connector assembly including an IDC, of an alternative preferred embodiment.

Several alternative IDC type connections are presented with reference to FIGS. 18 to 21. In FIG. 18, a variation of the IDC configuration described earlier is illustrated. In this embodiment, side portions 211 do not extend the entire length of the base portion 210. As a result, slots 212 do not extend the entire length of the base portion 210, and a receiving area 305 is created above the base portion and adjacent to the open end 213 of the slots. During manufacture of the end connector assembly, the IDC according to this embodiment is fitted before the heater wire(s) is (are) wound around the tube 200. Initially as the wires are first wound, they are located in receiving area 305 and are not engaged with slots 212. In order to complete the electrical connections, the wire(s) are subsequently pushed longitudinally with respect to conduit 200 (in direction of arrow 306) into slots 212 whereby the insulation on the wires is penetrated and electrical connection is completed. The secondary process of pushing the wire(s) into the slots may be accomplished by features on the cuff of end connector adapted to push the wire(s) into engagement during fitting. With the wires secure (preferably aided by cuff 216), the tube 200 can be cut to length before finally the end connector 205 can be fitted to complete the assembly. Alternatively, the secondary process of pushing the wire(s) into the slots may be accomplished by features on the cuff and/or end connector adapted to push the wire(s) into engagement during fitting. In this embodiment the IDC element is essentially stationary, and the wires are pushed into engagement to complete the circuit. This method requires the IDC to be fitted during the (otherwise) continuous tube manufacturing sequence. Sheathing (if desired) can be performed after the IDC installation and wire winding.

Figure 17:
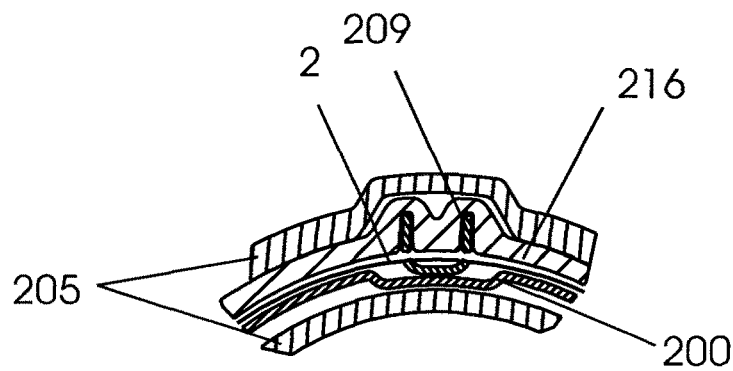
Figure 19:
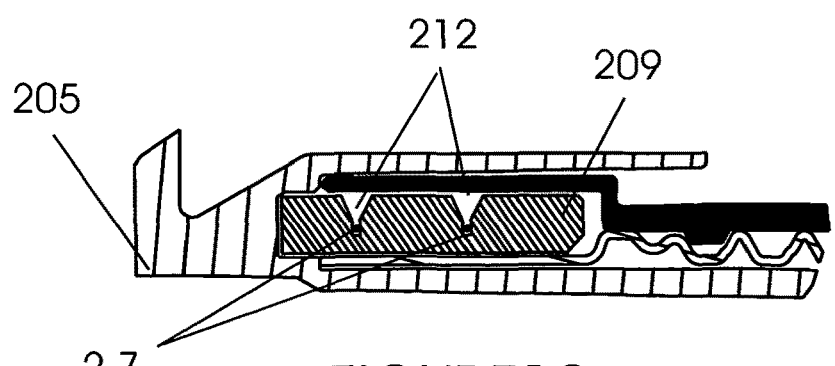
FIG. 19 is a side cross-section view (through the web of the IDC) of an end connector assembly of a further alternative preferred embodiment.
Figure 22:
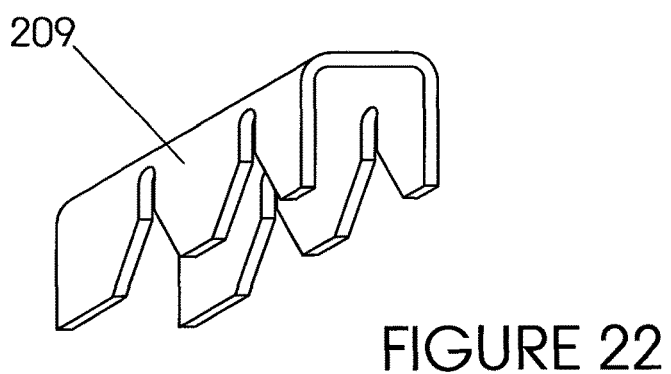
FIG. 22 is a perspective view of an IDC element of FIGS. 19-21.

In FIGS. 17, 19 & 22, a further IDC embodiment is illustrated sharing a similar basic structure as those described above. However, in this embodiment IDC 209 includes slots 212 arranged radially with respect to the conduit 200 and facing outwards. During manufacture the IDC 209 is positioned first and the wire(s) are wound directly over slots 212 thereby retaining the IDC in position. The wire(s) are then subsequently forced into the slot to displace the insulation and complete electrical connection.

The secondary process of pushing the wire(s) into the slots may be accomplished or aided by features on the cuff adapted to push the wire(s) into engagement during fitting. This is illustrated in FIG. 17.

With the wires secure (preferably aided by cuff 216), the tube 200 can then be cut to length before finally the end connector 205 is fitted to complete the assembly. In this embodiment the IDC element is essentially stationary, and the wires are pushed into engagement to complete the circuit.

Figure 20:
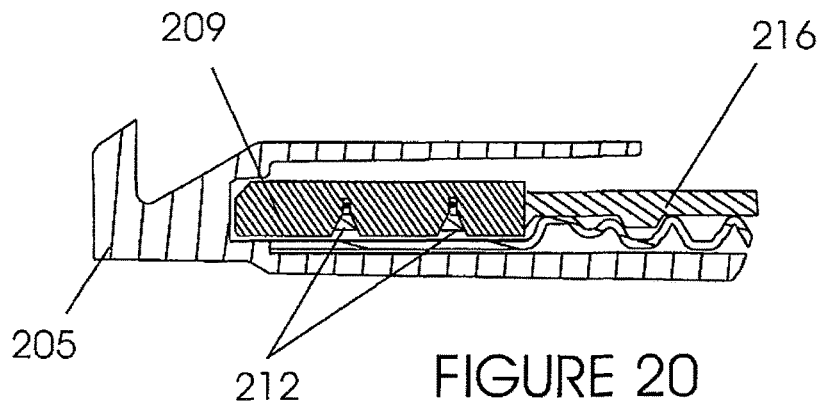
FIG. 20 is a side cross-section view of an end connector assembly of a further alternative preferred embodiment.
Figure 21:
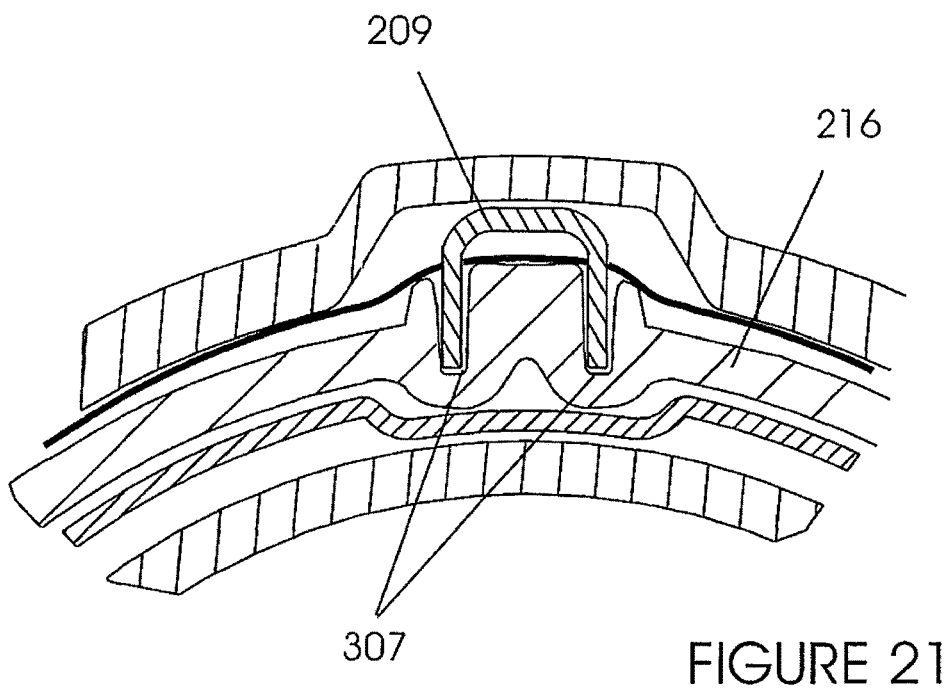
FIG. 21 is an end cross section view of the connector assembly of FIG. 20.

In FIGS. 20-22, a still further IDC termination embodiment is illustrated sharing the same basic IDC structure as that described above and illustrated in FIG. 22. In this embodiment IDC 209 includes slots 212 arranged radially with respect to the conduit 200 and positioned facing inwards. During manufacture the wires are wound first and the IDC is subsequently pushed over the wires. In order to allow the slots 212 to be pushed around the wires to complete the electrical connection, the wires need to be supported. Support is provided by the cuff 216 which in this embodiment is positioned under the IDC element as illustrated in FIG. 21. The cuff is positioned before the wires are wound over the top. Cuff 216, includes slots 307 correspondingly shaped to receive IDC 209. Alternatively, the conduit 200 may be formed with features in this region to support the wires and facilitate the pressing of the IDC over the wire to complete connection without requiring a separate cuff piece 216. With the wires secure, the tube 200 can then be cut to length before finally the end connector 205 can be fitted to complete the assembly. In this embodiment the wires are essentially stationary, and the IDC is pushed into engagement to complete the circuit. Sheathing (if desired) can be performed after the IDC installation and wire winding. Alternatively, the sheath (if present) can be fitted to the tube 200 before the IDC and then the IDC can be punched through the sheath to complete the electrical connection. Such an embodiment preferably utilises an IDC with sheath piercing features such as sharp edges or points.

Figure 23:
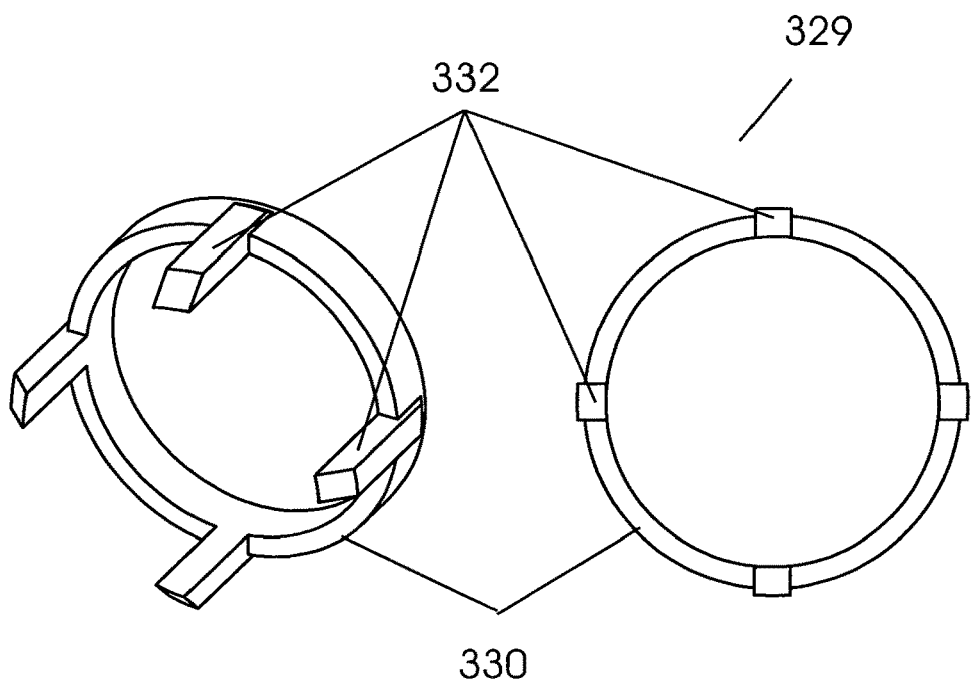
FIG. 23 is a perspective and plan view of an alternative form of wire support.

With particular reference to FIG. 23, a further embodiment of an IDC type connector termination method and associated wire support will be described. Wire support member 329 comprises a ring shaped body 330 having an inner radius approximately equal to the inner radius of the medical tube to which it is intended to fit. The ring member 330 includes at least one (and preferably a plurality) of wire support fingers 332 extending parallel with the axis of the annular body 330. The wire support fingers 332 (when there are more than one) are spaced around the perimeter of the ring body. Preferably, the spacing is even. Alternatively, a non-regular spacing may be adopted.

The purpose of the wire support member 329 is to support the wire(s) in channel or recess 208 away from the outer surface of the tube 200, so that the wire is not displaced when the IDC is pressed on. This embodiment of wire support is for use with the IDC member shown in FIG. 22, when inserted in a direction that is radially inwards as shown in the embodiments of FIGS. 20 and 21. Further, if an outer sheath is present, the wire support 329, provides support for the IDC to punch through the sheath and make the electrical connection.

Figure 24:
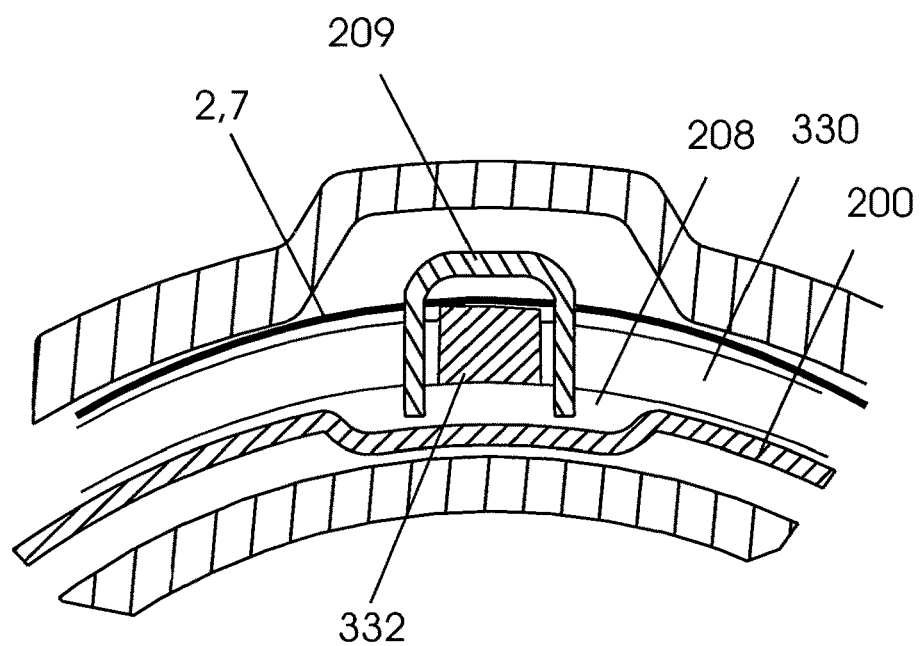
FIG. 24 is an end cross section view of the wire support of FIG. 23 shown in place on a medical conduit with end connector.

FIG. 24 illustrates a cross-section of a medical tube (and end connector) assembly with the wire support 329 in position. Wire support fingers project endways over the tube such that the fingers 332 are positioned directly underneath wires 2, 7. The IDC 209 is then pressed radially inwards until the electrical connections are made between one or more wires. The end connector is then subsequently fitted onto the end of the medical tube. Preferably, the end connectors include a channel 223 to accommodate the IDC as shown.

This design allows the wire winding, sheathing (if present) and trimming of the medical tube to length to be performed before the IDC is fitted. The IDC can be punched through the sheath (if present).

Figure 25:
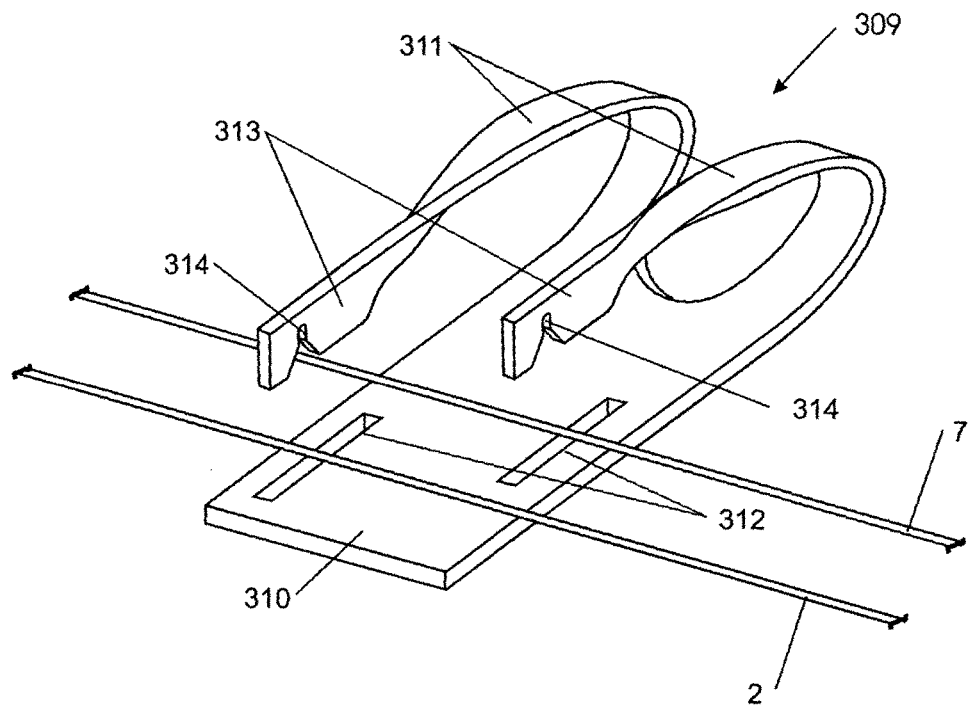
FIG. 25 is a perspective view of an IDC element according to a further embodiment.
Figure 27:
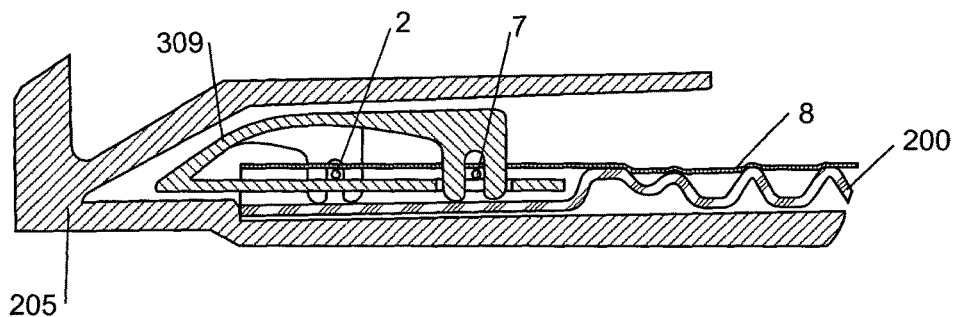
FIG. 27 is a side cross-section view of the IDC element of FIG. 25 shown assembled into an end connector.

With reference to FIGS. 25 & 27, a further embodiment of an IDC type connector will be described. In this embodiment IDC 309 takes the form of a spring clip comprising base 310 and resilient arms 311. Each of resilient arms 311 include at their respective ends a wire engaging portion 313, including insulation displacement slots 314. Preferably, the base 310 and arms 311 are formed from a single piece of metal as illustrated so that arms 311 are resiliently deformable with respect to the base 310. Alternatively, the arms may be separate parts and may be separately hinged and biased away from the base. Base 310 includes apertures 312 positioned (and shaped) to each receive (and in some embodiments retain) a wire engaging portion of respective arms 311 as the arm is moved toward the base.

IDC element 309 is configured to allow wire engaging portions 313 to pierce through the outer insulating sheath 8 and engage wires 2, 7 underneath via insulation displacement slots 314. An advantage with this embodiment is that the sheath 8 can be fitted over the conduit and cover the wires before the IDC element is installed. When assembling the conduit (after cutting to length) the IDC element can be positioned and inserted endways and pressed through the sheath to make connection with the wires just before the end connector 205 is installed. Alternatively, the end connector 205, is shaped such that installation onto the end of the tube 200 causes the IDC element to squash down and pierce the sheath and complete the electrical connection. The ends of the conduit 200 can be formed with features to suspend the wire(s) over a trough to allow the IDC to be located above and below. In this embodiment, the end connector maintains the wire engaging portions 313 on the wire. Alternatively (or in addition), the apertures 312 may capture and retain the wire engaging portions once pressed inside.

Figure 26:
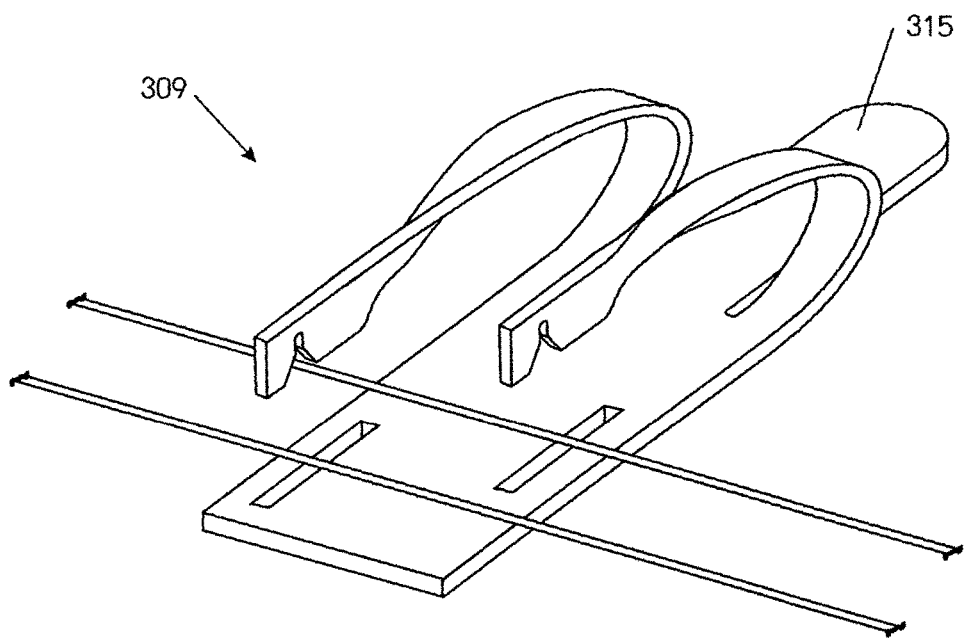
FIG. 26 is a perspective view of a variation of the IDC element of FIG. 25 including a connection pin.

In FIG. 26 a variation of the IDC element on FIGS. 25 & 27 is illustrated. In this embodiment, IDC 309 includes a connection pin 315 extending from base 310 which can be used for connecting to other parts of the circuit, for example to a power source. The pin 315 may be used as a soldering surface or may directly form a pin for connecting to a plug etc.

Figure 28A:
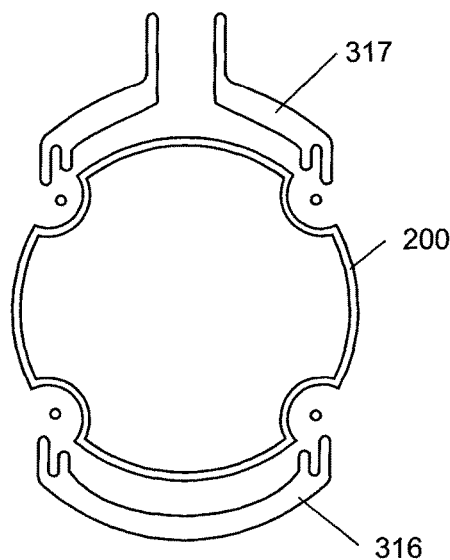
FIG. 28a is an end view of the machine end of a conduit showing an alternative IDC element configuration.
Figure 28B:
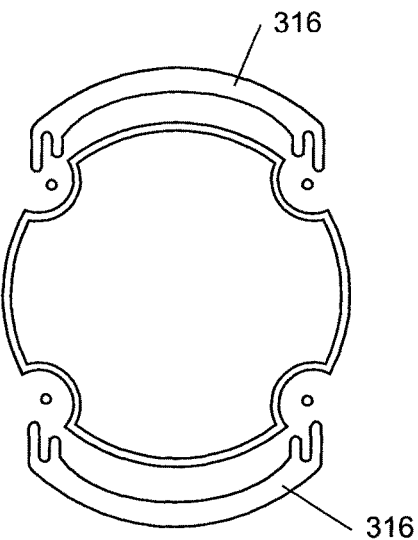
FIG. 28b is an end view of the patient end of the conduit of FIG. 28a showing the IDC element configuration.
Figure 29:
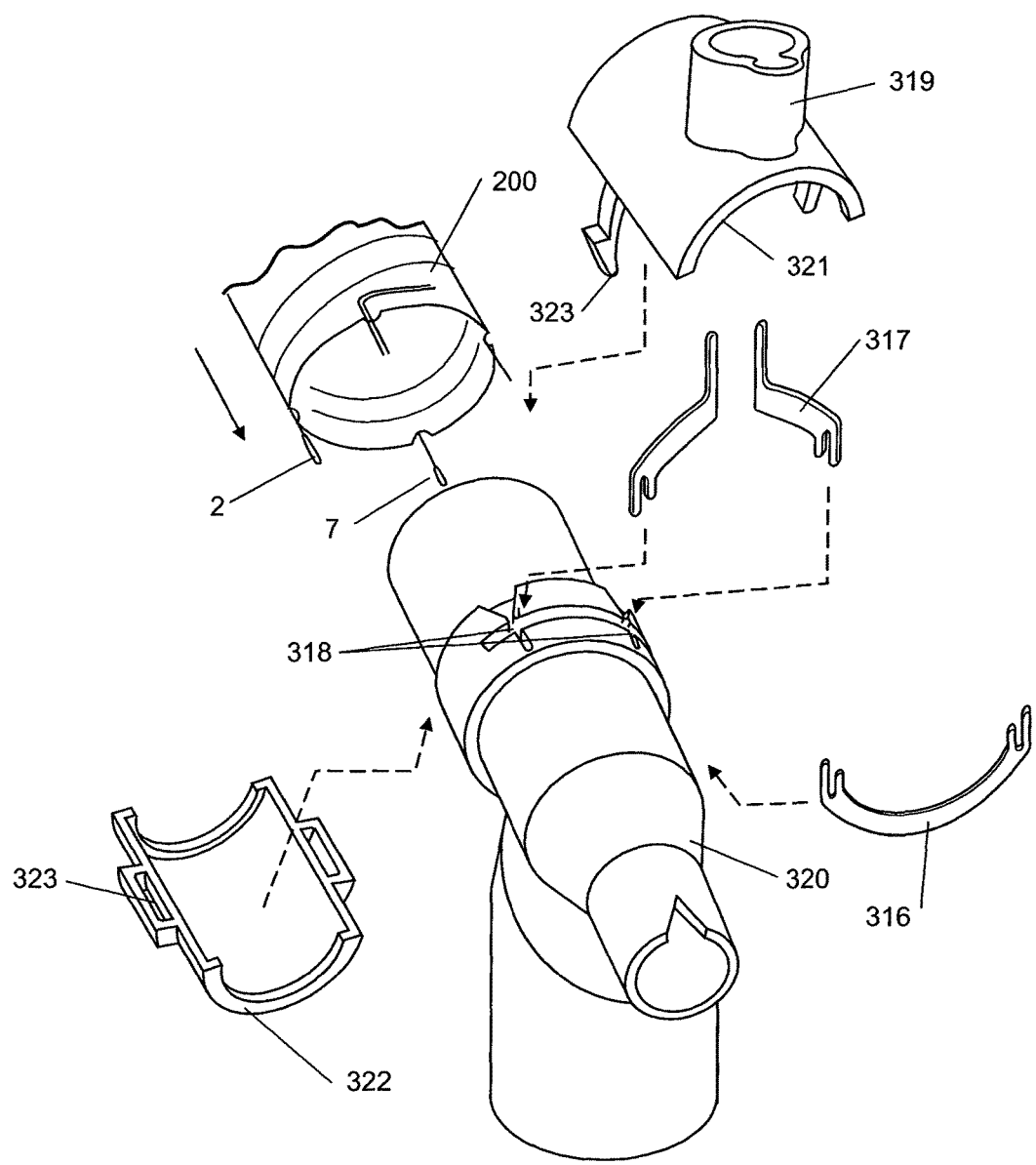
FIG. 29 is a perspective exploded assembly view of an end connector assembly incorporating IDC elements of FIG. 28.

With reference to FIGS. 28 & 29 a further alternative form of IDC type connection will now be described. In this embodiment the IDC element extends a substantial portion of the circumference of the conduit in order to electrically connect the wires wrapped around the conduit. These ring type IDC elements are illustrated in the schematic wiring diagrams of FIGS. 11a & 11c.

In the illustrated example embodiment four runs of wire are wrapped around the conduit 200 in a multi-helix arrangement. Each run of wire is spaced around the circumference by 90 degrees. Semi-ring type IDC elements 316 are inserted onto the wires in a radial direction to complete the electrical connection. Pin IDC elements 317 provide direct connection points for a plug for example and are supported by plug socket 319 in top housing 321.

To assemble the component, tube 200 is fitted over elbow 320 and the wires (2, 7) are extended through slots 318. Terminating ring 316 and pin elements 317 are inserted from below and above respectively into the slots 318 provided in the elbow 320 and engage with the wires to complete the electrical connections. Top and bottom housings 321, 322 respectively are snapped over the elbow 320 via snap features 323 and firmly anchor the IDC elements 316, 317 in position.

Preferred materials for manufacturing the medical tubing of the invention are Linear Low Density Polyethylene (LLDPE), Low Density Polyethylene (LDPE), Polypropylene (PP), Polyolefin Plastomer (POP), Ethylene Vinyl Acetate (EVA) or blends of these materials. Plasticised PVC may also be a suitable material, but it is not as well accepted for environmental reasons.

Preferred materials for the heater wires are copper, aluminium or a PTC (positive temperature coefficient) type material. Aluminium is not as conductive as copper, but may be an economical choice even though the wire diameter is larger for the same resistance. While the applied circuit voltage is intrinsically safe (less than 50V), for corrosion resistance and best electrical safety in the event of the tube or sheath being damaged, the wire will ideally be self insulated, either by enamel coating or anodising in the case of aluminium. Alternatively an extruded plastic sheath can be fitted. The insulation displacement elements described above will vary in dimension according to the gauge of wire and characteristics of insulation used so that they can effectively displace the insulation and reliably form a connection with the conductor wire.

The term "substantially uniform" wall thickness corrugated tube is intended to mean a tube having a corrugation profile wherein an outer peak, for example, comprises the maximum outside radius of the tube while also forming the maximum inner radius of the tube and an inner trough, for example, forms the minimum inner and outer radius of the tube. This type of tube is typically formed from a substantially uniform thickness extrusion that is subsequently corrugated. It will be appreciated that the subsequently formed corrugations may vary the wall thickness of the outer peak regions vs. inner the trough regions of the finished tube. The ratio of minimum to maximum actual wall thickness may vary as much as 1:1.5-3.0 for example.

Component of an Insufflation System

Laparoscopic surgery, also called minimally invasive surgery (MIS), or keyhole surgery, is a modern surgical technique in which operations in the abdomen are performed through small incisions (usually 0.5-1.5 cm) as compared to larger incisions needed in traditional surgical procedures. The abdomen is usually insufflated with carbon dioxide gas to create a working and viewing space.

Surgical procedures frequently involve electrosurgery or electrocautery or increasingly the use of lasers. The use of these devices tends to create surgical smoke in the working space due to burning of tissue. Smoke evacuation systems which use a discharge arm or limb are commonly used to remove the smoke from the surgical site, so that a surgeon can see what he or she is doing, and so that this potentially harmful material does not remain within the body cavity post-surgery. One end of the discharge arm or limb is connected to, or inserted into, a second incision (or sometimes the same incision). A typical smoke evacuation system generally includes a trocar and a cannula at the end to aid insertion into the operative site. The smoke exits the insufflated abdominal area through a discharge limb. It is desirable for the CO2 or other insufflation gas to be humidified before they are passed into the abdominal cavity. This can help prevent 'drying out' of the patient's internal organs, and can decrease the amount of time needed for recovery from surgery.

The present medical tubing may also find application to the delivery limb and/or especially the discharge limb of an insufflation system.

The foregoing description of the invention includes preferred forms thereof. Modifications may be made thereto without departing from the scope of the invention To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Preferred Features 1.1 A medical tube comprising:
   a tube wall and having a first end and a second end,
   at least one heater wire wrapped around said wall,
   near or at one of said first end or said second end, at least one recess in the outer surface of said wall, and wherein said heater wire passes over said at least one tube recess such that said wire does not contact the wall in the area of said tube recess.

1.2 A medical tube as claimed in claim 1.1, wherein said wall is helically corrugated with alternating crests and troughs; and
   said wall defining a least one helical track on an outer surface extending between said first and second ends, and
   said at least one heater wire is located in said at least one track.

1.3 A medical tube as claimed in claim 1.2, wherein at least one of said at least one tracks are associated with a crest of said corrugated wall.

1.4 A medical tube as claimed in claim 1.2, wherein at least one of said at least one tracks are associated with a trough of said corrugated wall.

1.5 A medical tube as claimed in any preceding claim wherein said tube further includes
an end connector on at least one of said first end or said second end.

1.6 A medical tube as claimed in any preceding claim, wherein said tube recess includes an insulation displacement connector therein and said insulation displacement connector is engaged on at least one said heater wire.

1.7 A medical tube as claimed in claim 1.6, wherein the end connector includes at least one connector recess aligned with said at least one tube recess.

1.8 A medical tube as claimed in claim 1.7, wherein said insulation displacement connector is located at least partially in said connector recess.

1.9 A medical tube as claimed in any of the preceding claims, wherein said tube includes more than one helical track, and each said helical track includes at least one heater wire.

1.10 A medical tube as claimed in claim 1.9, wherein said tube recess includes an insulation displacement connector therein and said insulation displacement connector is engaged on at least two said heater wires.

1.11 A medical tube as claimed in any preceding claim further including an outer sheath.

1.12 A medical tube as claimed in claim 1.11, wherein said sheath is supported on said crests.

1.13 A medical tube as claimed in one of claims 1.2 to 1.12, wherein at least one end of said tube further comprises a transition region in which said helical corrugation transitions to a semi-annular corrugation near the end of the tube.

1.14 A medical tube as claimed in claim 1.13, wherein said transition and semi-annular corrugation region provides a track for each said heater wire.

1.15 A medical tube as claimed in any one of claims 1.2 to 1.4, wherein said tube includes at least one pinch feature in said track to capture and retain a respective heater wire in said track.

1.16 A medical tube as claimed in any preceding claim, wherein said tube includes at least one locating feature near an end, said locating feature extending radially away from said tube.

1.17 A medical tube as claimed in claim 1.16, wherein said locating feature includes an undercut to at least partially capture said wire.

1.18 A medical tube as claimed in claim 1.16 or claim 1.17, wherein said locating feature is near a patient end.

1.19 A medical tube as claimed in any one of claims 1.16 to claim 1.17, wherein said feature is on said wall of said tube.

1.20 A medical tube as claimed in any one of claims 1.16 to claim 1.17, wherein said tube includes an end connector and said locating feature is on said end connector.

1.21 A medical tube as claimed in any one of claims 1.6 to 1.20, wherein said tube further includes a wire support member at an end of said tube, said wire support member comprising;
a ring shaped body having at least one wire support finger extending parallel with an axis of said ring body, and
said wire support finger is located in said recess such that said wire support finger is between an outer surface of said tube and said wire and supports said wire in said recess away from said tube.

1.22 A medical tube as claimed in claim 1.21 when dependent on claim 1.6, wherein said insulation displacement element is fitted over said wire support finger when engaging said wire.

1.23 A medical tube as claimed in any one of claims 1.2 to 1.22, wherein said wire support member includes a plurality of wire support fingers extending parallel with an axis of said ring body and spaced around the perimeter of said member.

1.24 A medical tube as claimed in claim 1.23, wherein said tube includes a plurality of said recesses and each of said plurality of wire support fingers is located in a respective recess.

1.25 A medical tube as claimed in claim 1.24, wherein there is a said insulation displacement element in each said recess and fitted over a respective said wire support finger.

2.1 A medical tube comprising:
a tube wall and having a first end and a second end,
at least two runs of heater wire wrapped around said wall in a multi helix arrangement,
at least one insulation displacement bridging element located near said first end and extending over a portion of the circumference of said tube, said bridging element engaging two or more said runs to complete at least part of an electrical circuit.

2.2 A medical tube as claimed in claim 2.1, wherein said wall is at least double helically corrugated with alternating crests and troughs defining a least two helical tracks on the outer surface extending between said first and second ends, and said at least two heater wire runs are located in a respective track.

2.3 A medical tube as claimed in claim 2.1 or claim 2.2, wherein said tube further comprises:
at least one insulation displacement terminal element located near said second end and extending over a portion of the circumference of said tube, said terminal element engaging only one of said runs and providing a terminal of said circuit.

2.4 A medical tube as claimed in claim 2.3, wherein said terminal is one of:
a. a spade terminal,
b. a pin terminal,
c. a socket terminal,
d. a loop terminal.

2.5 A medical tube as claimed in any of claims 2.1 to 2.4 wherein said tube further comprises at least one further insulation displacement bridging element located near said second end and extending over a portion of the circumference of said tube, said bridging element engaging two or more said runs to complete at least part of an electrical circuit.

2.6 A medical tube as claimed in any one or more of claims 2.1 to 2.5, wherein said tube further comprises an end connector on at least one of said first end or said second end,
said end connector receiving and retaining one or more of said insulation displacement elements.

2.7 A medical tube as claimed in claim 2.6 when dependent on claim 2.3, wherein said end connector includes a socket aperture adapted to receive said insulation displacement terminal elements.

3.1 An insulation displacement element comprising:
a channel body having a base and two side portions,
a pair of aligned slots from a first open end,
said slots shaped to displace outer insulation from a wire or wires pushed into said slots.

3.12 The insulation displacement element as claimed in claim 3.1, wherein the pair of slots extend lengthwise of the body.
3.13 The insulation displacement element as claimed in claim 3.1, wherein the element comprises a pair of aligned slots extending lengthwise of the body from a first open end and separating said two side portions from said base for a portion of the length of said body.
3.14 The insulation displacement element as claimed in claim 3.1, wherein the pair of slots extend perpendicular to the base.
3.15 An insulation displacement element comprising:
a channel body having a base and two side portions,
a pair of aligned slots extending lengthwise of the body from a first open end and separating said two side portions from said base for a portion of the length of said body,
said slots shaped to displace outer insulation from a wire or wires pushed into said slots.
3.2 An insulation displacement element as claimed in any one of claims 3.1 to 3.15, wherein said base and/or side portions are chamfered or shaped to guide a wire into engagement with said slots.
3.3 An insulation displacement element as claimed in any one of claims 3.1 to 3.2, wherein said channel body has a substantially "U" shaped cross section.
3.4 An insulation displacement element as claimed in claim 3.3, wherein said "U" shape has a substantially flat bottom.
3.5 An insulation displacement element as claimed in any one of claims 3.1 to 3.4, wherein a second end of said channel body is adapted to engage with a plug or socket.
3.6 An insulation displacement element as claimed in claim 3.5, wherein said base includes at said second end a slot extending lengthwise of said body for a portion of the length of the body.
3.7 An insulation displacement element as claimed in any one of claims 3.1 to claim 3.4, wherein said base at said open end projects beyond said side portions.
3.8 An insulation displacement element as claimed in any one of claims 3.1 to 3.7, wherein each said side portion includes more than one aligned slot for receiving more than one wire.
4.1 An insulation displacement element comprising:
a channel body having a base and two depending side portions,
a pair of aligned slots, one in each side portion, extending perpendicular to the base from a first open end,
said slots shaped to displace outer insulation from a wire or wires pushed into said slots.
4.2 An insulation displacement element as claimed in claim 4.1, wherein said side portions are chamfered or shaped to guide a wire into engagement with said slots at said open end.
4.3 An insulation displacement element as claimed in claim 4.1 or 4.2, wherein said channel body has a substantially "U" shaped cross section.
4.4 An insulation displacement element as claimed in claim 4.3, wherein said "U" shape has a substantially flat bottom.
4.5 An insulation displacement element as claimed in any one of claims 4.1 to 4.4, wherein a first end of said channel body is adapted to engage with a plug or socket and said base at said first end projects beyond said side portions.
4.6 An insulation displacement element as claimed in claim 4.5, wherein said base includes at said first end a slot extending lengthwise of said body for a portion of the length of the base.
4.7 An insulation displacement element as claimed in any one of claims 4.1 to 4.6, wherein each said side portion includes more than one aligned slot for receiving more than one wire.
5.1 An insulation displacement element comprising:
a base,
an arm including a wire engaging portion resiliently attached to said base such that said wire engaging portion can be resiliently urged towards said base,
said wire engaging portion including at least one slot shaped to displace outer insulation from a wire or wires pushed into said slot.
5.2 An insulation displacement element as claimed in claim 5.1, wherein said element includes more than one said arm.
5.3 An insulation displacement element as claimed in claim 5.1 or 5.2, wherein said base further includes at least one aperture shaped to receive a corresponding at least one said arm.
5.4 An insulation displacement element as claimed in any one of claims 5.1 to 5.3, wherein said base and said arms are formed from a single piece of material.
5.5 An insulation displacement element as claimed in any one of claims 5.1 to 5.3, wherein said base and said arms are formed separately, and
said arms are pivotally connected to said base and biased to a position away from said base.
5.6 An insulation displacement element as claimed in claims 5.4, wherein said material is a sheet material and said arms are bent back on said base.
5.7 An insulation displacement element as claimed in claims 5.3, wherein said apertures are shaped to retain respective wire engaging portions after being received.
5.8 An insulation displacement element as claimed in any one of claims 5.1 to 5.7, wherein said element further comprises a terminal portion depending from said base.
6.1 A medical tube connector comprising:
a tubular body having a longitudinal axis,
a collar extending from part way along said body and defining an annular gap between an outer surface of said body and an inner surface of said collar,
said annular gap adapted to receive a tube fitted over said body and under said collar to form a substantial seal,
said collar further comprising at least one open ended pocket adapted to receive an insulation displacement type element in a direction substantially parallel with said axis of said body.
6.2 A medical tube connector as claimed in claim 6.1, wherein said collar further comprises retaining features for retaining a medical tube.
6.3 A medical tube connector as claimed in claim 6.1 or claim 6.2, wherein said body is substantially straight.
6.4 A medical tube connector as claimed in any one of claims 6.1 to claim 6.3, wherein said body is an 'elbow'.
6.5 A medical tube connector as claimed in any one of claims 6.1 to claim 6.4, wherein said body includes at least one port adapted for receiving a sensor.
6.6 A medical tube connector as claimed in any one of claims 6.1 to claim 6.5, wherein at least one said pocket is open on each end.
7.1 A retaining collar comprising:
a plurality of semi-annular segments joined in series.

7.2 A retaining collar as claimed in claim 7.1, wherein one or more of said segments include a retaining feature on an external surface.

7.3 A retaining collar as claimed in claim 7.1 or claim 7.2, wherein one or more of said segments include a retaining feature on an internal surface.

7.4 A retaining collar as claimed in any one of claims 7.1 to 7.3, wherein one or more of said segments include an open ended pocket adapted to receive an insulation displacement element.

7.5 A retaining collar as claimed in any one of claims 7.1 to 7.4, wherein said segments are joined by any one or more of;
   a) living hinges,
   b) complementary hook and eye attachment
   c) adhesive strips
   d) straps
   e) clamps.

8.1 A method of terminating a medical tube comprising:
   taking a medical tube and winding at least one insulated wire around an outer surface from at least substantially one end to the other,
   capturing said wire so that it is substantially stationary with respect to said tube, and
   pushing at least one insulation displacement element over said wire to complete an electrical connection.

8.2 A method of terminating a medical tube as claimed in claim 8.1 wherein, said tube includes a recess in the outer wall, and said insulation displacement element is located at least partially in said recess after installation.

8.3 A method of terminating a medical tube as claimed in claim 8.1 or 8.2, wherein tube includes more than one insulated wire wound around an outer surface from at least substantially one end to the other.

8.4 A method of terminating a medical tube as claimed in claim 8.3, wherein said insulation displacement element is engaged over at least two insulated wires to electrically connect parts of an electrical circuit.

8.5 A method of terminating a medical tube as claimed in claim 8.2, wherein said insulation displacement element is located entirely in said recess after installation.

8.6 A method of terminating a medical tube as claimed in any one of claims 8.1 to claim 8.5, wherein said step of capturing said wire includes fitting a retaining collar over an end of said conduit.

8.7 A method of terminating a medical tube as claimed in claim 8.6, wherein said collar is the collar of any one or more of claims 7.1 to 7.4.

8.8 A method of terminating a medical tube as claimed in any one of claims 8.1 to 8.7, wherein said step of capturing said wire includes fitting an end connector over an end of said conduit.

8.9 A method of terminating a medical tube as claimed in any one of claims 8.1 to 8.8, wherein said method includes pushing more than one insulation displacement element over said wire to join parts of an electrical circuit.

8.10 A method of terminating a medical tube as claimed in any one of claims 8.1 to 8.9, wherein said insulation displacement element is as claimed in any one or more of claims 3.1 to 5.8.

8.11 A method of terminating a medical tube as claimed in claim 8.8, wherein said end connector is as claimed in any one or more of claims 6.1 to 6.6.

8.12 A method of terminating a medical tube as claimed in any one of claims 8.1 to 8.11, wherein said method further includes fitting a sheath over the outer surface of said tube and over said wire.

8.13 A method of terminating a medical tube as claimed in any one of claims 8.1 to claim 8.12, wherein said medical tube is as claimed in any one or more of claims 1.1 to 2.7.

8.14 A method of terminating a medical tube as claimed in any one of claims 8.2 to claim 8.13, wherein a wire support member is fitted to said tube to support said wire before the step of pushing said insulation displacement element over said wire.

8.15 A method of terminating a medical tube as claimed in claim 8.14, wherein said wire support element comprises:
   a ring shaped body having at least one wire support finger extending parallel with an axis of said ring body, and
   said wire support finger is located in said recess such that said wire support finger is between an outer surface of said tube and said wire and supports said wire in said recess away from said tube.

8.16 A method of terminating a medical tube as claimed in claim 8.15, wherein said insulation displacement element is fitted over said wire support finger when engaging said wire.

8.17 A method of terminating a medical tube as claimed in claim 8.15 or 8.16, wherein said wire support member includes a plurality of wire support fingers extending parallel with an axis of said ring body and spaced around the perimeter of said member.

8.18 A method of terminating a medical tube as claimed in claim 8.17, wherein said tube includes a plurality of said recesses and each of said plurality of wire support fingers is located in a respective recess.

8.19 A medical tube as claimed in claim 8.18, wherein there is a said insulation displacement element in each said recess and fitted over a respective said wire support finger.

10.1 A method of terminating a medical tube substantially as herein described and with reference to any one or more of the drawings.

10.2 A method of terminating a medical tube substantially as herein described and using any one or more of the components claimed in any one of the preceding claims.

10.3 A method of forming a medical tube substantially as herein described and with reference to any one or more of the drawings.

10.4 A method of assembling a medical tube substantially as herein described and using any one or more of the components claimed in any one of the preceding claims.

10.5 A medical tube assembly substantially as herein described and with reference to any one or more of the drawings 10.6 A medical tube assembly substantially as herein described and using any one or more of the components claimed in any one of the preceding claims.

The invention claimed is:

1. A medical tube comprising:
   a tube wall comprising a first end and a second end,
   a heater wire wrapped around said tube wall, and
   near or at one of said first end or said second end, a tube recess in an outer surface of said tube wall, wherein said tube recess extends parallel to an axis extending through said tube from said first end to said second end, and
   said heater wire passes over said tube recess such that said heater wire does not contact said tube wall in the area of said tube recess.

2. A medical tube as claimed in claim 1, wherein said tube wall further comprises helical corrugations with alternating crests and troughs, said tube wall defines a helical track on said outer surface extending between said first end and said second end, and said heater wire is located in said helical track.

3. A medical tube as claimed in claim 2, wherein said helical track is associated with said crests.

4. A medical tube as claimed in claim 2, wherein said helical track is associated with said troughs.

5. A medical tube as claimed in claim 1 further comprising an end connector on at least one of said first end and said second end.

6. A medical tube as claimed in claim 1 further comprising an insulation displacement connector located at least partially in said tube recess, wherein said insulation displacement connector is engaged on said heater wire.

7. A medical tube as claimed in claim 6 further comprising an end connector on at least one of said first end and said second end, wherein said end connector comprises a connector recess aligned with said tube recess.

8. A medical tube as claimed in claim 7, wherein said insulation displacement connector is located at least partially in said connector recess.

9. A medical tube as claimed in claim 2 further comprising more than one heater wire and more than one helical track, wherein at least one of said more than one heater wire is located in each of said more than one helical track.

10. A medical tube as claimed in claim 9 further comprising an insulation displacement connector located at least partially in said tube recess, wherein said insulation displacement connector is engaged on at least two of said more than one heater wire.

11. A medical tube as claimed in claim 1 further comprising an outer sheath.

12. A medical tube as claimed in claim 11, wherein said tube wall comprises helical corrugations with alternating crests and troughs and said sheath is supported on said crests.

13. A medical tube as claimed in claim 2, wherein said tube wall further comprises a transition region near one of said first end or said second end in which said helical corrugations transition to semi-annular corrugations.

14. A medical tube as claimed in claim 13, wherein said transition region and said semi-annular corrugations each define a track for said heater wire.

15. A medical tube as claimed in claim 14 further comprising a pinch feature in said track to capture and retain said heater wire in said track.

16. A medical tube as claimed claim 1 further comprising a locating feature near one of said first end or said second end, said locating feature extending radially away from said medical tube.

17. A medical tube as claimed in claim 16, wherein said locating feature comprises an undercut to at least partially capture said heater wire.

18. A medical tube as claimed in claim 16, wherein said locating feature is near a patient end of said medical tube.

19. A medical tube as claimed in claim 16, wherein said locating feature is on said tube wall.

20. A medical tube as claimed in claim 16 further comprising an end connector, wherein said locating feature is on said end connector.

21. A medical tube as claimed in claim 6 further comprising a wire support member at one of said first end or said second end, said wire support member comprising
   a ring shaped body comprising a wire support finger extending parallel with an axis of said ring shaped body, wherein
   said wire support finger is located in said tube recess such that said wire support finger is between said outer surface and said heater wire and supports said heater wire in said tube recess away from said outer surface.

22. A medical tube as claimed in claim 21, further comprising an insulation displacement connector located at least partially in said tube recess, wherein said insulation displacement connector is fitted over said wire support finger and engaged on said heater wire.

23. A medical tube as claimed in claim 21, wherein said wire support member comprises a plurality of wire support fingers extending parallel with the axis of said ring shaped body and spaced around a perimeter of said wire support member.

24. A medical tube as claimed in claim 23 further comprising a plurality of tube recesses, wherein each of said plurality of wire support fingers is located in a respective one of said plurality of tube recesses.

25. A medical tube as claimed in claim 24 further comprising a plurality of insulation displacement connectors, wherein each of said plurality of insulation displacement connectors is located in a respective one of said plurality of tube recesses and fitted over a respective one of said plurality of wire support fingers.

* * * * *